US008071293B2

(12) United States Patent
High et al.

(10) Patent No.: US 8,071,293 B2
(45) Date of Patent: Dec. 6, 2011

(54) PRRG4-ASSOCIATED COMPOSITIONS AND METHODS OF USE THEREOF IN METHODS OF TUMOR DIAGNOSIS

(75) Inventors: Katherine A. High, Merion, PA (US); Fayaz R. Khazi, Swedesboro, NJ (US); Kirk Chu, Narberth, PA (US); Luca Monaldini, Turate (IT); Mustafa Naci Yazicioglu, Drexel Hill, PA (US); Samuel Murphy, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 12/480,426

(22) Filed: Jun. 8, 2009

(65) Prior Publication Data

US 2010/0017897 A1 Jan. 21, 2010

Related U.S. Application Data

(63) Continuation-in-part of application No. PCT/US2007/086995, filed on Dec. 10, 2007.

(60) Provisional application No. 60/869,218, filed on Dec. 8, 2006.

(51) Int. Cl.
*C12Q 1/68* (2006.01)
(52) U.S. Cl. .......................................................... 435/6
(58) Field of Classification Search ..................... 435/6
See application file for complete search history.

(56) References Cited

U.S. PATENT DOCUMENTS

| 2006/0019256 A1 | 1/2006 | Clarke et al. |
| 2007/0117164 A1 | 5/2007 | Raskov et al. |

OTHER PUBLICATIONS

Smith et al. (Nature Biotechnology 15:1222-1223 (1997)).*
Brenner (Trends in Genetics 15:132-133 (1999)).*

* cited by examiner

*Primary Examiner* — Lynn Bristol
(74) *Attorney, Agent, or Firm* — Dann, Dorfman, Herrell & Skillman; Kathleen D. Rigaut

(57) ABSTRACT

Compositions and methods for detecting PRRG4- and PRRG2 associated molecules are provided as are methods of use thereof for the detection and treatment of cancer.

15 Claims, 18 Drawing Sheets

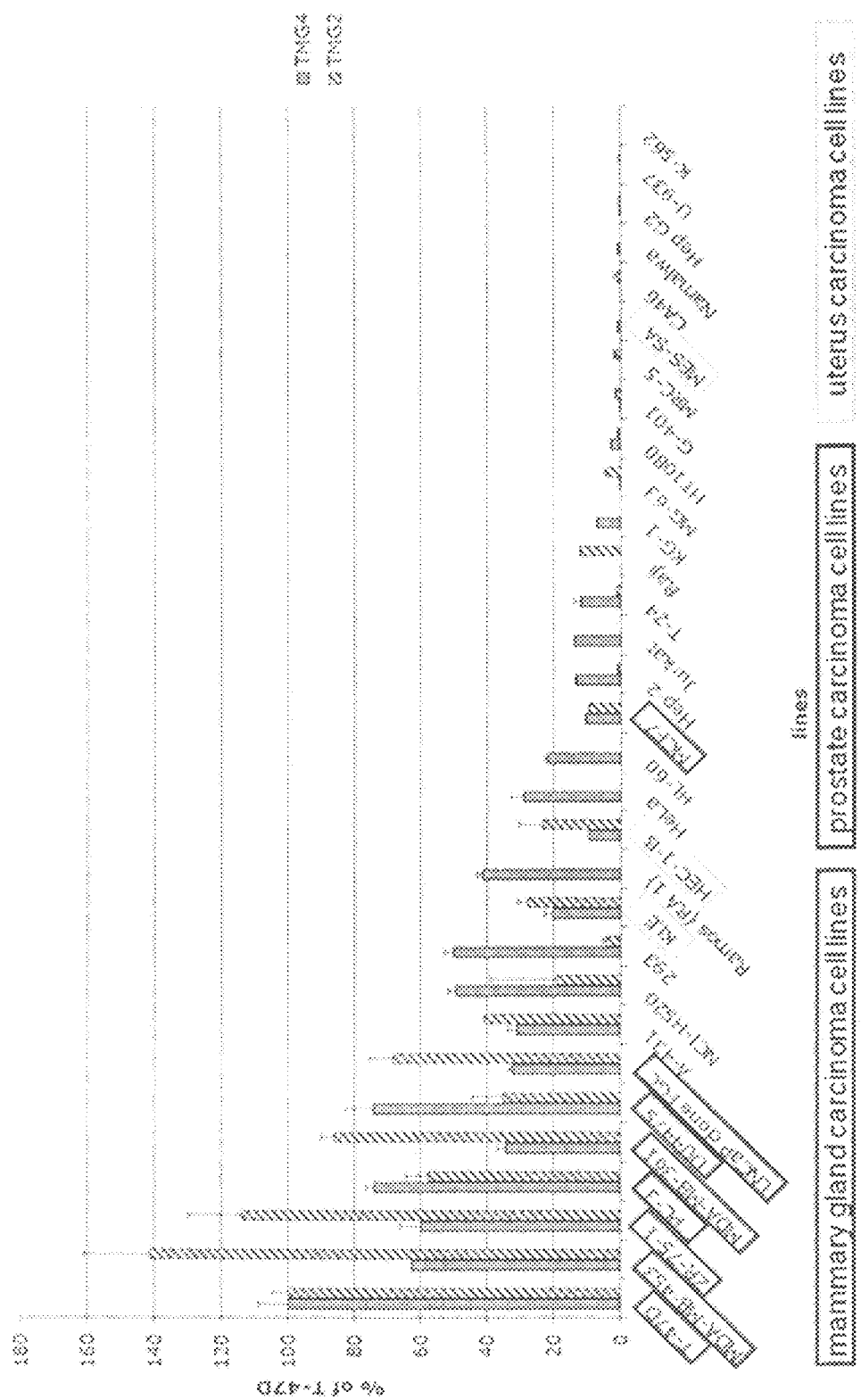

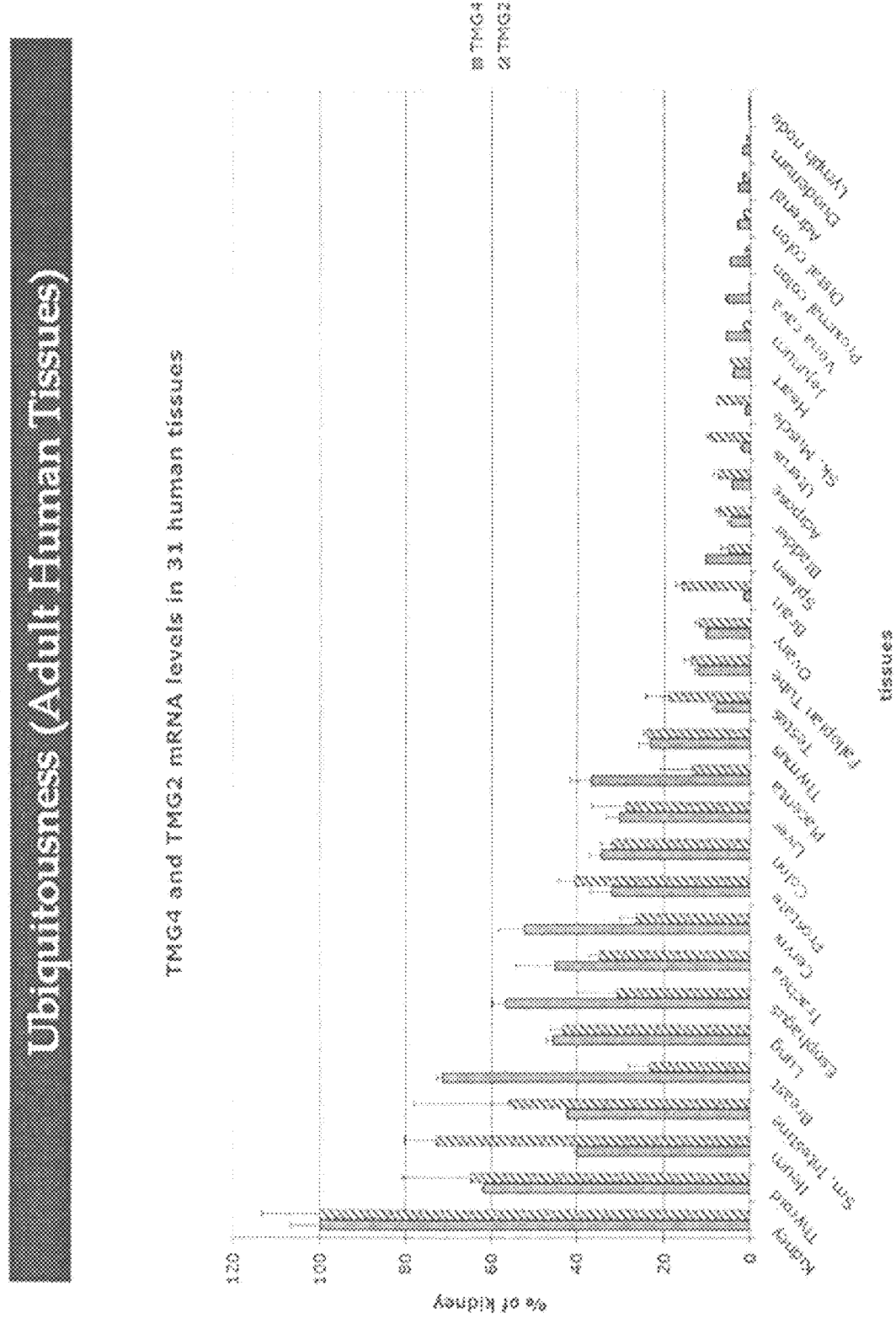

ERK P

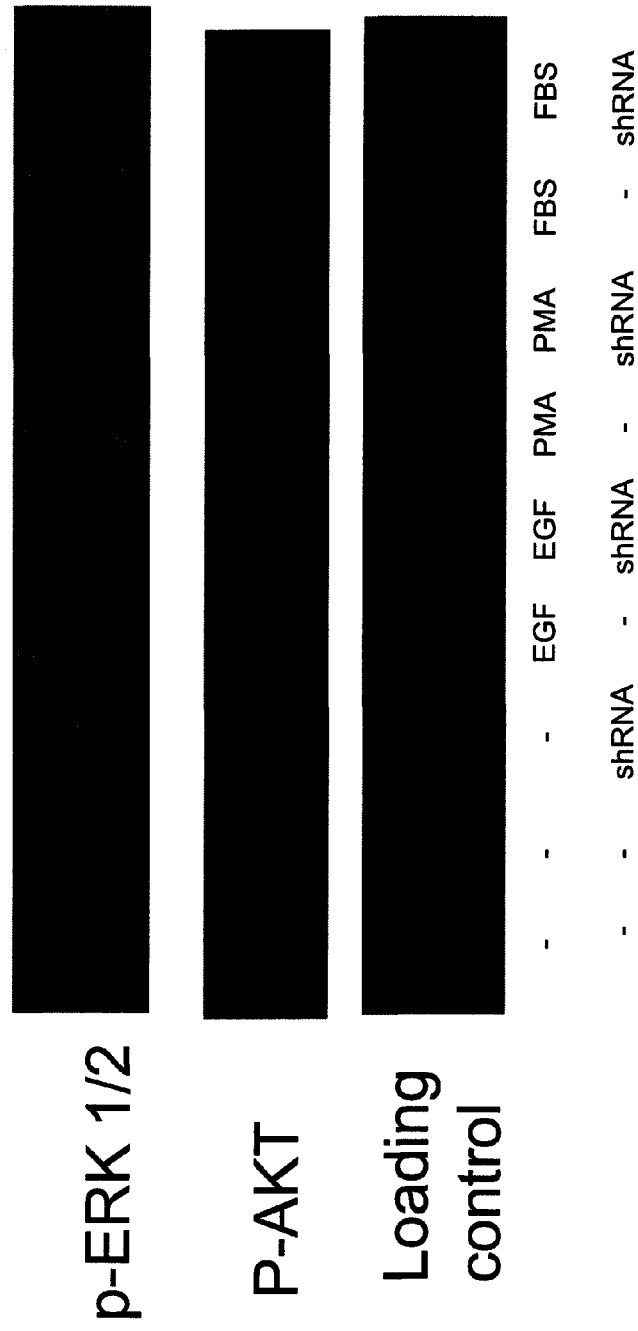

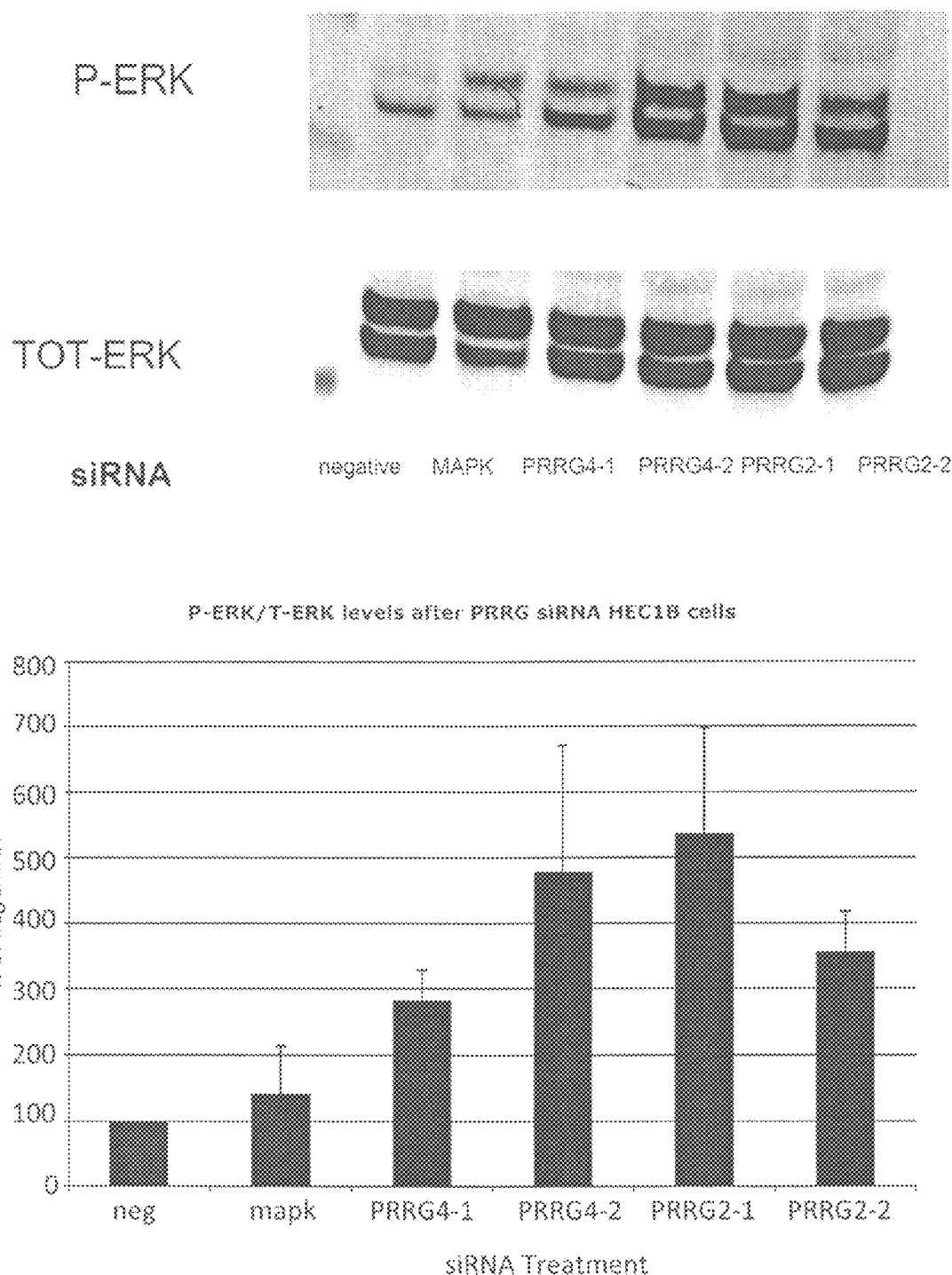

Figure 6A
PRRG4 Probed with WW Array I

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| A | SMURF1-D1 | | SMURF1-D2 | | SMURF1-D3 | | SMURF1-D4 | | WWP1-D1 | | WWP1-D2 | | WWP1-D3 | | WWP1-D4 | | pos | |
| B | WWP2-D3 | | WWP2-D4 | | NEDD4-D1 | | NEDD4-D2 | | NEDD4-D3 | | NEDD4-D4 | | NEDD4L-D1 | | NEDD4L-D2 | | pos | |
| C | NEDD4L-D3 | | NEDD4L-D4 | | NEDL1-D1 | | NEDL1-D2 | | caveolin-3 | | KIAA 1301 | | BAG3 | | PABPN1 | | pos | |
| D | GAS7 | | YAP1 | | C20orf16 | | BAIAP1-D1 | | BAIAP1-D2 | | JM26 | | ARHGAP 9 | | MAGI-3-D1 | | pos | |
| E | MAGI-3-D2 | | LOC 201176 | | FNBP4 | | GST | | | | | | | | | | pos | |
| F | pos | | pos | | pos | | pos | | pos | | pos | | pos | | pos | | pos | |

Schematic diagram of the TranSignal WW Domain Array I. The proteins on the array are spotted in duplicate at 100 ng. Histidine-tagged ligand has been spotted along the bottom (row F) and in duplicated along the right side (columns 17, 18) of the membrane. These spots are intended for alignment. Note that the notch is at the top right-hand corner.

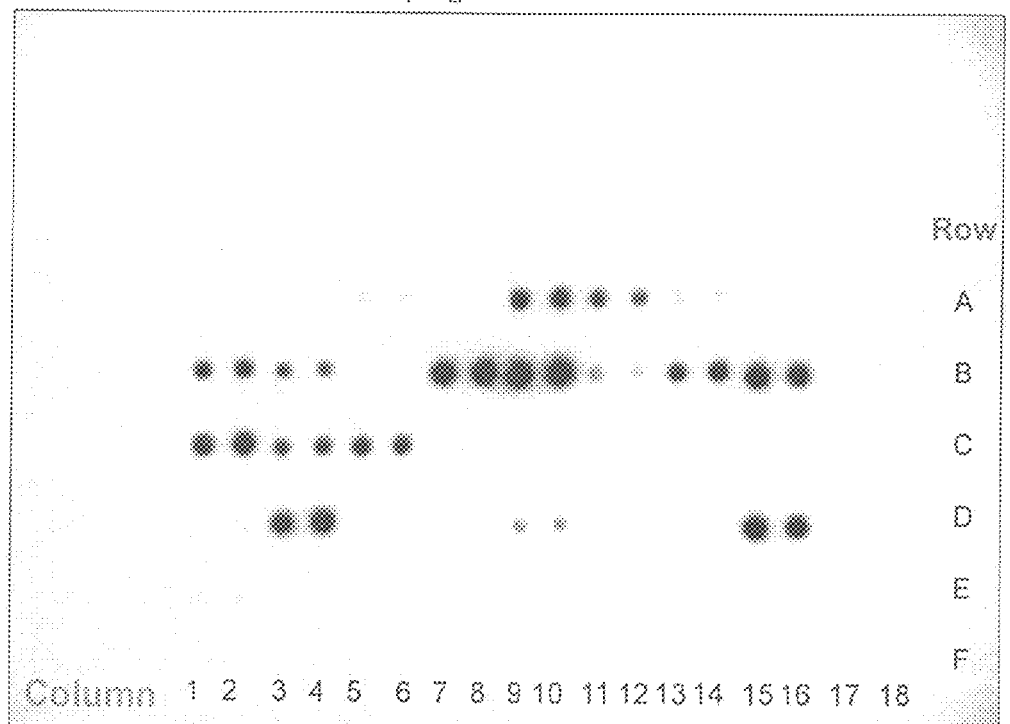

Figure 6B
PRRG4 Probed with WW Array II

|   | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| A | AIP1-D2 | | ITCH-D1 | | ITCH-D2 | | ITCH-D3 | | ITCH-D4 | | DRP2 | | DMO | | UTRN | | pos | |
| B | FNBP4 | | bA45824 | | WBP4-D1 | | WBP4-D2 | | APBB1 | | APBB2 | | APBB3 | | HYPC-D1 | | pos | |
| C | HYPC-D2 | | HYPA-D1 | | HYPA-D2 | | HYPB | | PIN1 | | PIN1L | | IQGAP2 | | TCERG1-D1 | | pos | |
| D | TCERG1-D2 | | TAZ | | WWOX-D1 | | WWOX-D2 | | ARHGAP12 | | PEPP2 | | SAV1-D2 | | SAV1-D1 | | pos | |
| E | GST | | | | | | | | | | | | | | | | pos | |
| F | pos | | pos | | pos | | pos | | pos | | pos | | pos | | pos | | pos | |

Schematic diagram of the TranSignal WW Domain Array II. The proteins on the array are spotted in duplicate at 100 ng. Histidine-tagged ligand has been spotted along the bottom (row F) and in duplicated along the right side (columns 17, 18) of the membrane. These spots are intended for alignment. Note that the notch is at the top right-hand corner.

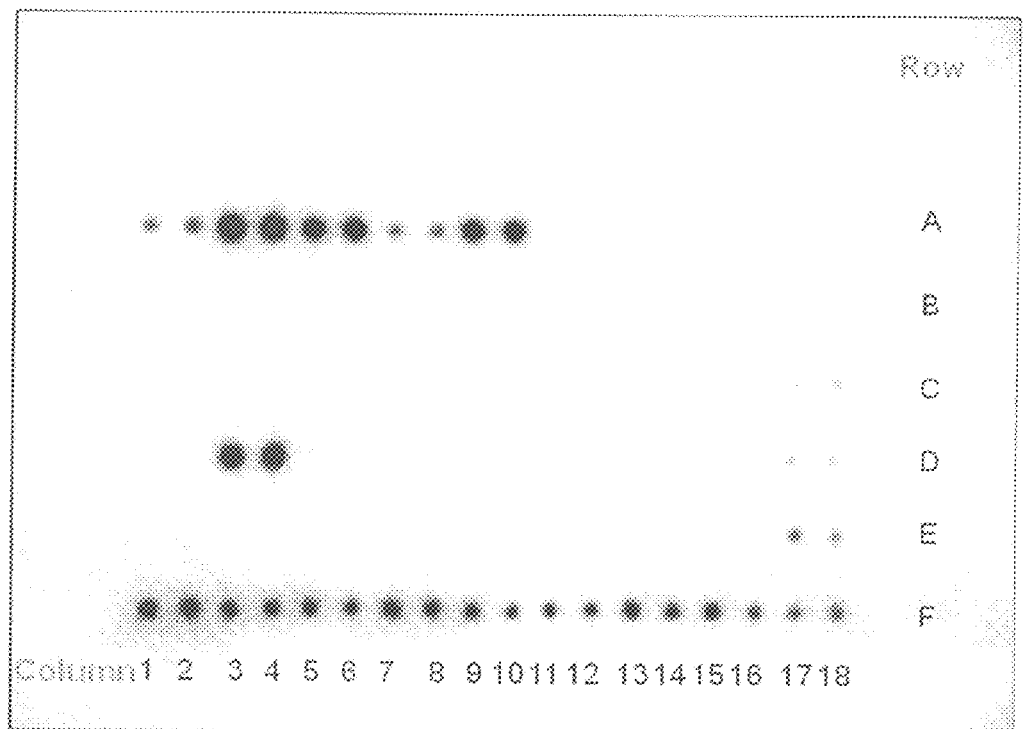

Figure 8A

```
LOCUS       NM_024081    2015 bp    mRNA    linear    PRI
17-NOV-2006

DEFINITION  Homo sapiens proline rich Gla (G-carboxyglutamic acid) 4

(transmembrane) (PRRG4), mRNA.

ACCESSION   NM_024081

VERSION     NM_024081.4  GI:40255027

KEYWORDS    .

SOURCE      Homo sapiens (human)

ORGANISM  Homo sapiens

Eukaryota; Metazoa; Chordata; Craniata; Vertebrata;
Euteleostomi;

Mammalia; Eutheria; Euarchontoglires; Primates; Haplorrhini;

Catarrhini; Hominidae; Homo.

REFERENCE   1  (bases 1 to 2015)

AUTHORS   Kulman,J.D., Harris,J.E., Xie,L. and Davie,E.W.

TITLE     Identification of two novel transmembrane gamma-
carboxyglutamic acid proteins expressed broadly in fetal and adult tissues JOURNAL   Proc. Natl. Acad. Sci. U.S.A. 98 (4), 1370-1375 (2001)

PUBMED   11171957

COMMENT     PROVISIONAL REFSEQ: This record has not yet been subject to
final

NCBI review. The reference sequence was derived from
BC063393.1. On Dec 20, 2003  this sequence version replaced gi:34147609.

FEATURES         Location/Qualifiers
  source     1..2015

/organism="Homo sapiens"
```

Figure 8A (continued)

/mol_type="mRNA"

/db_xref="taxon:9606"

/chromosome="11"

/map="11p13"

gene      1..2015

/gene="PRRG4"

/note="proline rich Gla (G-carboxyglutamic acid) 4 (transmembrane); synonym: TMG4"

/db_xref="GeneID:79056"

/db_xref="HGNC:30799"

/db_xref="HPRD:15187"

CDS      254..934

/gene="PRRG4"

/go_component="extracellular region; integral to membrane [PMID 11171957]; membrane"

/go_function= "calcium ion binding"

/note="transmembrane gamma-carboxyglutamic acid protein 4;

/codon_start=1

/product="proline rich Gla (G-carboxyglutamic acid ) 4 (transmembrane)"

4 precursor"

/protein_id="NP_076986.1"

/db_xref="GI:13129074"

Figure 8A (continued)

/db_xref="CCDS:CCDS7881.1"

/db_xref="GeneID:79056"

/db_xref="HGNC:30799"

/db_xref="HPRD:15187"

/translation="MFTLLVLLSQLPTVTLGFPHCARGPKASKHAGEEVFTSKEEANF
FIHRRLLYNRFDLELFTPGNLERECNEELCNYEEAREIFVDEDKTIAFWQEYSAKGPT
TKSDGNREKIDVMGLLTGLIAAGVFLVIFGLLGYYLCITKCNRLQHPCSSAVYERGRH
TPSIIFRRPEEAALSPLPPSVEDAGLPSYEQAVALTRKHSVSPPPPYPGHTKGFRVFK
KSMSLPSH"

STS      1129..1724

/gene="PRRG4"

/standard_name="GDB:434012"

/db_xref="UniSTS:157204"

ORIGIN

```
  1 cccggaccga ggcaggacct cacccccgcgc gtgttccccg ggcgcccctc tgcgaaccccc
 61 aggcccttcc caggtttgcg cgcgggggcc atccagaccc tgcggagagc gaggcccgga
121 gcgtcgccga ggtttgaggg cgccggagac cgagggcctg gcggccgaag gaaccgcccc
181 aagaagagcc tctggcccgg gggctgctgg aacatgtgcg gggggacaca gtttgtttga
241 cagttgccag actatgttta cgcttctggt tctactcagc caactgccca cagttaccct
301 gggggtttcct cattgcgcaa gaggtccaaa ggcttctaag catgcgggag aagaagtgtt
361 tacatcaaaa gaagaagcaa acttttcat acatagacgc cttctgtata atagatttga
421 tctggagctc ttcactcccg gcaacctaga aagagagtgc aatgaagaac tttgcaatta
481 tgaggaagcc agagagattt ttgtggatga agataaaacg attgcatttt ggcaggaata
541 ttcagctaaa ggaccaacca caaaatcaga tggcaacaga gagaaaatag atgttatggg
```

Figure 8A (continued)

```
 601 ccttctgact ggattaattg ctgctggagt atttttggtt attttggat tacttggcta 661 ctatctttgt atcactaagt gtaataggct acaacatcca tgctcttcag ccgtctatga 721 aaggggagg cacactccct ccatcatttt cagaagacct gaggaggctg ccttgtctcc 781 attgccgcct tctgtggagg atgcaggatt accttcttat gaacaggcag tggcgctgac 841 cagaaaacac agtgtttcac caccaccacc atatcctggg cacacaaaag gatttagggt 901 atttaaaaaa tctatgtctc tcccatctca ctgactacct tgtcattttg gtataagaaa 961 tttgtgttat ttgataggcc gggcatggtg gctcatgcct gtaatcccag cactttggga 1021 ggccaggagt tcgagaccag cctggccaac atggtgaaac ccggtctcta ctaaaaattc 1081 aaaaattacc taggcgtcat ggggcatgcc tgtagtccca cctacttggg aggctgaagc 1141 aggagaattg ctcgaacctg ggaggcagag gttgcagtaa gctgagatca cgccactgca 1201 ttccagcctg ggcgacagag caagactcca tctcaaaaat aaaataaaaa aagaaagaaa 1261 gaaaagaaga agaaaagaga agaaggagaa ggagatgaag gaggaggagg aggagaagga 1321 gaagaagaag aagaagaaga ccacaaaaga catgactatc caacttttta tgacaaactg 1381 caaggaataa aggaagaata agtccatgta ctgtaccaca gaagttctgt ctgcatcttg 1441 gacctgaact tgatcattat cagcttgata agagactttt tgactctata tccttgcagt 1501 taagaagaaa gcactttttt gtaatgtttg ttttaatggt tcaaaaaaaa tctttcttat 1561 aaagagcata ggtagaatta gtgaactctt tggatccttt gtacagataa aggttataga 1621 tttcttgtgt tgaatattaa aaagcaagg atgtctaacc attaagatta tccaaagtca 1681 ggctgggcgc agtggctcac gcctgtaatc ccagcacttt gggagggata ggtgggcgga 1741 tcacctgagg tcaggagttt gagaccagcc tggccaacat ggcaaaaccc cgtctctaca 1801 aaaatacaaa agaaattagc cagacatgat ggcgggtgcc tctaatccca gctactgggg 1861 aggctgaggt gggagaatcg cttgaactcg ggaggtggag gttgtagtga ggcgagattg 1921 tgccattgca ctccaacctg ggcgacagag tgagactcca tctcaaaaaa aaaaaaaaa 1981 aaaaaaaaaa aaaaaaaaa aaaaaaaaaa aaaaa
```

Figure 8B

```
LOCUS       NM_000951               1411 bp    mRNA    linear   PRI 26-OCT-2008
DEFINITION  Homo sapiens proline rich Gla (G-carboxyglutamic acid) 2 (PRRG2),
            mRNA.
ACCESSION   NM_000951
VERSION     NM_000951.2  GI:209870060
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (bases 1 to 1411)
  AUTHORS   Kulman,J.D., Harris,J.E., Xie,L. and Davie,E.W.
  TITLE     Proline-rich Gla protein 2 is a cell-surface vitamin K-dependent
            protein that binds to the transcriptional coactivator
            Yes-associated protein
  JOURNAL   Proc. Natl. Acad. Sci. U.S.A. 104 (21), 8767-8772 (2007)
   PUBMED   17502622
  REMARK    GeneRIF: PRGP2 may be involved in a signal transduction pathway,
            the impairment of which may be an unintended consequence of
            warfarin therapy
REFERENCE   2  (bases 1 to 1411)
  AUTHORS   Fu,G.K., Wang,J.T., Yang,J., Au-Young,J. and Stuve,L.L.
  TITLE     Circular rapid amplification of cDNA ends for high-throughput
            extension cloning of partial genes
  JOURNAL   Genomics 84 (1), 205-210 (2004)
   PUBMED   15203218
REFERENCE   3  (bases 1 to 1411)
  AUTHORS   Kulman,J.D., Harris,J.E., Xie,L. and Davie,E.W.
  TITLE     Identification of two novel transmembrane gamma-carboxyglutamic
            acid proteins expressed broadly in fetal and adult tissues
  JOURNAL   Proc. Natl. Acad. Sci. U.S.A. 98 (4), 1370-1375 (2001)
   PUBMED   11171957
REFERENCE   4  (bases 1 to 1411)
  AUTHORS   Jolliffe,C.N., Harvey,K.F., Haines,B.P., Parasivam,G. and Kumar,S.
  TITLE     Identification of multiple proteins expressed in murine embryos as
            binding partners for the WW domains of the ubiquitin-protein ligase
            Nedd4
  JOURNAL   Biochem. J. 351 PT 3, 557-565 (2000)
   PUBMED   11042109
REFERENCE   5  (bases 1 to 1411)
  AUTHORS   Kulman,J.D., Harris,J.E., Haldeman,B.A. and Davie,E.W.
  TITLE     Primary structure and tissue distribution of two novel proline-rich
            gamma-carboxyglutamic acid proteins
  JOURNAL   Proc. Natl. Acad. Sci. U.S.A. 94 (17), 9058-9062 (1997)
   PUBMED   9256434
COMMENT     VALIDATED REFSEQ: This record has undergone validation or
            preliminary review. The reference sequence was derived from
            CD609900.1, AF009243.1 and CB851486.1.
            On Oct 22, 2008 this sequence version replaced gi:4506136.
            COMPLETENESS: complete on the 3' end.
PRIMARY     REFSEQ_SPAN         PRIMARY_IDENTIFIER PRIMARY_SPAN        COMP
            1-156               CD609900.1         8-163
            157-911             AF009243.1         1-755
            912-1411            CB851486.1         1-500               c
FEATURES             Location/Qualifiers
     source          1..1411
                     /organism="Homo sapiens"
                     /mol_type="mRNA"
                     /db_xref="taxon:9606"
                     /chromosome="19"
                     /map="19q13.33"
```

Figure 8B (continued)

```
gene            1..1411
                /gene="PRRG2"
                /gene_synonym="PRGP2"
                /note="proline rich Gla (G-carboxyglutamic acid) 2"
                /db_xref="GeneID:5639"
                /db_xref="HGNC:9470"
                /db_xref="HPRD:09189"
                /db_xref="MIM:604429"
exon            1..152
                /gene="PRRG2"
                /gene_synonym="PRGP2"
                /inference="alignment:Splign"
                /number=1
exon            153..250
                /gene="PRRG2"
                /gene_synonym="PRGP2"
                /inference="alignment:Splign"
                /number=2
CDS             166..774
                /gene="PRRG2"
                /gene_synonym="PRGP2"
                /note="proline-rich Gla (G-carboxglutamic acid)
                polypeptide 2; proline-rich Gla (G-carboxyglutamic acid)
                polypeptide 2"
                /codon_start=1
                /product="proline rich Gla (G-carboxyglutamic acid) 2"
                /protein_id="NP_000942.1"
                /db_xref="GI:4506137"
                /db_xref="CCDS:CCDS12773.1"
                /db_xref="GeneID:5639"
                /db_xref="HGNC:9470"
                /db_xref="HPRD:09189"
                /db_xref="MIM:604429"
                /translation="MRGHPSLLLLYMALTTCLDTSPSEETDQEVFLGPPEAQSFLSSH
                TRIPRANHWDLELLTPGNLERECLEERCSWEEAREYFEDNTLTERFWESYIYNGKGGR
                GRVDVASLAVGLTGGILLIVLAGLGAFWYLRWRQHRGQQPCPQEAGLISPLSPLNPLG
                PPTPLPPPPPPPPGLPTYEQALAASGVHDAPPPPYTSLRRPH"
exon            251..426
                /gene="PRRG2"
                /gene_synonym="PRGP2"
                /inference="alignment:Splign"
                /number=3
exon            427..466
                /gene="PRRG2"
                /gene_synonym="PRGP2"
                /inference="alignment:Splign"
                /number=4
exon            467..602
                /gene="PRRG2"
                /gene_synonym="PRGP2"
                /inference="alignment:Splign"
                /number=5
exon            603..755
                /gene="PRRG2"
                /gene_synonym="PRGP2"
                /inference="alignment:Splign"
                /number=6
STS             709..983
                /gene="PRRG2"
                /gene_synonym="PRGP2"
                /standard_name="PMC29263P1"
```

Figure 8B (continued)

```
                        /db_xref="UniSTS:272444"
       exon             756..1393
                        /gene="PRRG2"
                        /gene_synonym="PRGP2"
                        /inference="alignment:Splign"
                        /number=7
       STS              813..1325
                        /gene="PRRG2"
                        /gene_synonym="PRGP2"
                        /standard_name="PRRG2_8571"
                        /db_xref="UniSTS:468619"
ORIGIN
        1 gccagaaacg gggatcaggc ctggttaccg ggagtggggc gcccctcctc cttatcccct
       61 cccctcttcc ctgtcccctt tcacagctgg ctgtagctgg ccaaggagtt ctcgattaaa
      121 gaggaagggg cagtgctcac atttctgggc aggtgtctgg aaaatatgag gggccacccc
      181 tctctgctgc tgctatatat ggcattaacc acctgcctgg atacttcacc cagtgaggag
      241 acagaccaag aagtcttcct gggtccccca gaggcccaga gcttcctgag tagccatacc
      301 cggattccaa gagccaacca ctgggacctg gagctgctca caccagggaa cctggaacgg
      361 gagtgtctgg aagagaggtg ttcctgggaa gaggccaggg agtattttga ggacaacact
      421 ctcacggagc gcttttggga gagctacatc tacaatggca aggagggcg tggacgagtg
      481 gatgtggcca gcctggctgt ggggctgaca ggtggcatcc tgctcattgt cctggccggc
      541 ctgggagcct tttggtatcc gcgctggcga cagcaccgag gccagcagcc ctgtccccaa
      601 gaggccgggc tcattagccc tctgagtcct ttgaaccctc tgggcccacc gacgcccctg
      661 cctccacccc caccccacc cccaggcctc cccacctatg agcaggcgct ggcagcctct
      721 ggggtacacg acgcacctcc accccctac accagcctca ggaggcctca ctgaagagct
      781 gctttcgaga cccggctctc cgaaccgtgc ccctgattca taccggattc cggaagccgc
      841 taggcctcat agacgccgaa gctggacttg gagtggggaa tggtgggagt aggggtcatc
      901 cggcccgagg cctgccctgg cacacgcgtt tccgccgcgt atggatatac acatgttttc
      961 ggcaacgtgt tcccgtgtcc tggcccctca cgggcccccca cactctcctg accgtgaggg
     1021 cactggtcag ttccgcccccc gtggtaggca gacgcgcggg gaaattcgga cccaggagcc
     1081 cagccccggc tgtgccatct tgtgtatggg cagatatgac ctgacagccc cctccagtgc
     1141 cacagggtac gcacacgcag agcccccgcct gtgcacacgc gtgtcttcgt gcactccccg
     1201 tgcggtacag gggcacttcg taacccaggg aaagggcggg gggcatattt gcaagcgcgc
     1261 tcggtgcggg caggctcgca ttgcacccag ggagctggag ttgagctgtt ccctaaata
     1321 aaaacccttc ggaaaggaga ccaaaaaaag cagaaataat gcaaaaaata ataatgaaat
     1381 gaactgcgat cccaaaaaaa aaaaaaaaa a
//
```

PRRG4-ASSOCIATED COMPOSITIONS AND METHODS OF USE THEREOF IN METHODS OF TUMOR DIAGNOSIS

This application is a Continuation-in-part application of PCT/US2007/086995 filed 10 Dec. 2007, which in turn claims priority to U.S. Provisional Application 60/869,218 filed Dec. 8, 2006, both of the aforementioned applications being incorporated herein by reference herein as though set forth in full.

Pursuant to 35 U.S.C. §202(c) it is acknowledged that the U.S. Government has certain rights in the invention described, which was made in part with funds from the National Institutes of Health, Grant Number NIH-NIHLBI PO1 HL074124.

FIELD OF THE INVENTION

The present invention relates generally to the fields of molecular biology, oncology and gene, protein, or small molecule drug therapeutics. More particularly, it concerns the identification and functional characterization of proline-rich gamma-carboxyglutamic acid proteins prrg4 and prrg2 as proteins involved in tumorigenesis. The invention provides methods of utilizing PRRG4 and/or PRRG2 (TMG4 in older publications) proteins as biomarkers and diagnostic tools to detect malignancies in humans. Furthermore, the invention provides methods for the treatment or prevention of cancers based on therapeutic delivery of nucleic acids, polypeptides, or small molecules or their derivatives that alter the function of these proteins.

BACKGROUND OF THE INVENTION

Several publications and patent documents are cited throughout the specification in order to describe the state of the art to which this invention pertains. Each of these citations is incorporated by reference herein as though set forth in full.

Second only to heart disease, cancer is the leading cause of death in the United States, striking one in two men and one in three women (Landis, 1998). Normal tissue homeostasis is a highly regulated process of cell proliferation and cell death. Cancer development is the culmination of complex, multistep biological processes, occurring through the accumulation of genetic alterations resulting in an imbalance in the genes controlling either cell proliferation or cell death. Many if not all of these alterations involve specific cellular growth controlling genes that are mutated. These genes typically are classified as proto-oncogenes and tumor suppressor genes. Any event that leads to alterations of either class of genes leads to abnormal cell growth and can result in cancer.

Proto-oncogenes, upon dysregulation, induce uncontrolled cellular proliferation. Cellular levels of proto-oncogenes are an excellent diagnostic tool to assess the onset of cancer. Moreover, a detailed understanding of proto-oncogenes at a cellular level enables development of strategies for early detection and control of neoplastic tendencies. Upon detection, the dysregulated proto-oncogene can be corrected by various therapies (gene transfer, antibodies, small molecules or others) designed to block the function of the protein.

In vertebrates, proteins modified by gamma-glutamyl carboxylation fall into three major categories: vitamin-K dependent coagulation factors, coregulators of blood coagulation, and osteocalcin and matrix Gla proteins. PRRG4 is a single pass, type I transmembrane protein with a vitamin-K dependent γγ-carboxy-glutamic acid-rich domain (Kulman et al PNAS, 2001). Proline-rich gamma-carboxyglutamic acid protein 2, a paralog of PRRG4 is also widely expressed in many tissues. The function of these proteins is not known, nor are there any reports that suggest a relation to tumor formation.

SUMMARY OF THE INVENTION

In accordance with the present invention, PRRG4-related and PRRG2-related compositions and methods of use thereof in cancer detection are provided.

In one embodiment, a method of detecting a predisposition to cancer in a patient is disclosed. An exemplary method entails providing a biological sample from the patient; and detecting expression levels of a PRRG4-associated molecule and/or a PRRG2-associated molecule in the biological sample compared to normal control sample, samples exhibiting an alteration in expression levels of one or both proteins relative to the normal control sample, being indicative of an increased predisposition to cancer in said patient. The PRRG4- or PRRG2-associated molecule to be detected can include, without limitation, a PRRG4- or PRRG2-polypeptide or fragment, and PRRG4 or PRRG2 nucleic acids or fragments thereof.

Also provided in accordance with the present invention is a method for screening for substances which modulate the activity of a PRRG4 and/or PRRG2 polypeptide, the method comprising contacting at least one test substance with the polypeptide in a reaction medium, testing the activity of the treated PRRG4 or PRRG2 polypeptide and comparing that activity with the activity of native, untreated polypeptide(s) in a comparable reaction medium. In an alternative embodiment the screening assay described above can be performed in whole cells expressing PRRG4 and/or PRRG2.

In yet another aspect of the invention, transgenic animals which exhibit altered levels of PRRG4 or PRRG2 protein expression are provided. Mice which overexpress and underexpress PRRG4 or PRRG2 are provided herein. Such animals have utility in in vivo screening assays to identify agents which modulate PRRG4 or PRRG2 activity. Such agents may have efficacy in the treatment of cancer. Such in vivo screening assays are also within the scope of the invention.

BRIEF DESCRIPTION OF THE DRAWINGS

FIG. 2C is a graph showing expression levels of PRRG4 and PRRG2 in 31 different human cell lines. FIG. 2D is a graph showing PRRG4 and PRRG2 expression levels in 31 different human tissues.

FIG. 5B is a Western blot showing that there is cross talk between PRRG4 signaling pathways and other signaling pathways, such as those modulated by PMA, EGF, and FBS. FIG. 5C shows that silencing of either PRRG4 or PRRG2 significantly increases ERK phosphorylation in treated cells.

FIG. 6 provides data showing that PRRG4 interacts with several proteins involved in the regulation of cellular proliferation.

FIG. 8A provides GenBank Accession information for PRRG4. cDNA sequence is SEQ ID NO: 1. Protein sequence is SEQ ID NO:2. FIG. 8B provides GenBank Accession information for PRRG2. cDNA sequence is SEQ ID NO: 11. Protein sequence is SEQ ID NO: 12.

DETAILED DESCRIPTION OF THE INVENTION

Figure 1:
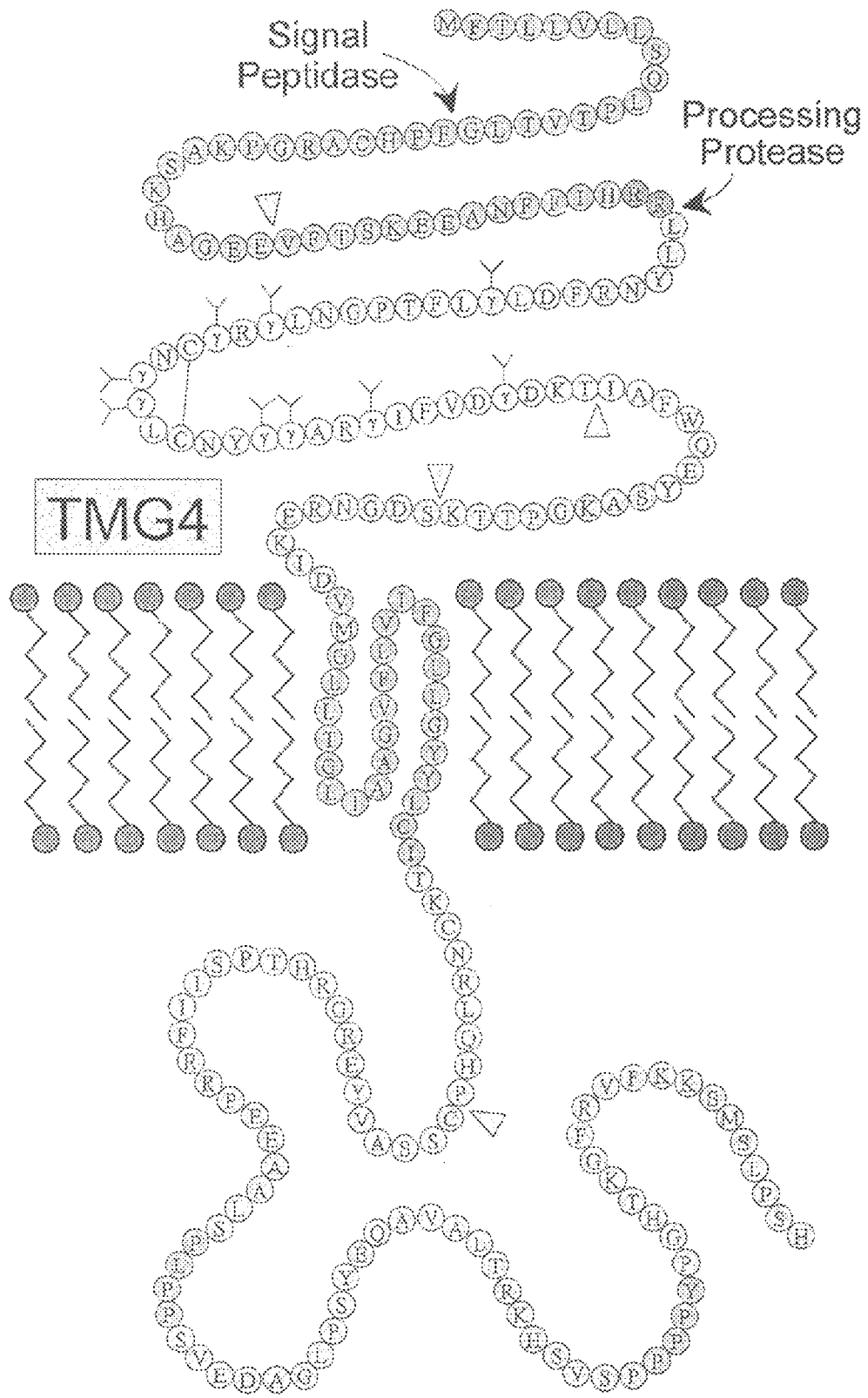
FIG. 1 is a schematic diagram of the PRRG4 transmembrane protein. PRRG4 has homology to vitamin K dependent clotting factors. The deduced amino acid sequence is 226 residues long (for the human protein). The protein consists of a N-terminal signal sequence (17 residues), a propeptide (36 residues) and a 43 residue long Gla domain. The putative transmembrane domain spans residues 114-138. The cytoplasmic domain contains a potential SH3 domain-binding motif PXXP in residues 176-179, and a possible WW domain interaction motif PPXY at residues 204-207. In humans, it is expressed in placenta, lung, liver, skeletal muscle, cervix, brain, kidney and other tissues. SEQ ID NO: 2 is shown.

Proline-rich gamma carboxyglutamic acid 4 (PRRG4 also referred to as TMG4 in the literature) is a single pass, type I transmembrane protein with a vitamin-K dependent gamma-carboxy-glutamic acid-rich domain (Kulman et al PNAS, 2001). PRRG2 is a paralog of PRRG4 present on chromosome 19. Bioinformatic analysis of the primary sequence indicates a very high degree of conservation (ca. 80%) among mammals and to-date no known functional roles have been assigned to this protein. In our efforts to elucidate molecular functions of PRRG4, we first analyzed sub cellular localization of this protein.

Microscopic analysis of HEK293T cells expressing a PRRG4-GFP fusion construct showed juxtanuclear localization of the tagged protein at 24 h post transfection. Staining with organelle specific fluorescent dyes revealed that the PRRG4-GFP primarily localizes to the trans Golgi network in the cell. Recently, there have been increasing numbers of reports of golgi-localized proteins participating in compartmentalized signal transduction pathways and affecting cell differentiation and proliferation by activating major signaling cascades like the Ras-Raf/MAPK signaling cascades. Moreover, the transmembrane localization and the current lack of evidence for a direct role for PRRG4 in the coagulation pathways encouraged us to hypothesize that PRRG4 may play a role in signal transduction. To test this we generated a PRRG4 over-expressing cell line (high-PRRG4) by stably transfecting HEK293T cells with a CMV-promoter driven PRRG4 plasmid, and a PRRG4 knock-down cell line (low-PRRG4) by transfections with a PRRG4 short-hairpin RNA (shRNA) expression vector. The levels of PRRG4 gene expression were confirmed in both the cell lines by RNA and protein expression analysis. The low-PRRG4 cells showed >90% knockdown of PRRG4 in comparison to untransfected control cells. The cells were grown under standard tissue culture conditions for 48 h after which they were harvested. Total cell lysates from the cell lines were analyzed by western blotting using primary antibodies against a panel of signal transduction proteins representing major signaling pathways including threonine kinase, tyrosine kinase and ERK2. The results showed no significant changes in activation of signal transduction proteins tested except for extracellular-signal-regulated kinase (ERK)-2. The high-TMG cells showed a down modulation of phosphorylated ERK2 while the low-PRRG4 cell lysates showed a 500-fold up regulation of phosphorylated ERK2 when compared to the levels in the low-PRRG4 cells.

Our observations were confirmed visually by assaying the cells for intracellular localization of ERK2. We used immunofluorescence staining to show that PRRG4 levels regulate ERK2 activation based on PRRG4 dependent translocation of ERK2 using anti phospho-ERK2 and anti-ERK2 antibodies. More than 85% of high-PRRG4 cells showed extra nuclear localization of ERK2 while phosphorylated ERK2 was localized in the nucleus in >80% of low-PRRG4 cells. Thus there is an inverse correlation between PRRG4 levels and ERK2 phosphorylation. We conclude that PRRG4 is a molecular modulator of ERK2. These studies suggest novel roles for vitamin-K dependent Gla-proteins in regulating cell growth and differentiation. We have also conducted two critical experiments; first, we generated mice that had reduced levels of murine PRRG4, owing to expression of a short hairpin RNA that specifically reduces levels of the transcript of this protein. These mice exhibited decreased litter size but were otherwise normal. Second, we made mice that overexpressed PRRG4. In this case, the gene was under the control of the CMV promoter, a ubiquitously expressed promoter. These mice appeared phenotypically normal until approximately 18 months of age. At this point, a number of the mice appeared ill. We sacrificed a total of 8 of the sickest mice and discovered that 7 had tumors. The tumors were in liver, lung, heart, kidney and spleen, and further histological studies are being conducted. This stands in contrast to the results of the mice with reduced expression of PRRG4. Of these mice, currently ranging in age from 4-15 months, none appear ill. Moreover, in a screen of older mice (N=23) in our colony with a mean age of 20.3 months none of them appeared to be ill.

DEFINITIONS

As used herein the phrase "PRRG4 associated molecule" refers to a PRRG4 (also known as TMG4) protein, polypeptide or fragment thereof. The phrase also encompasses PRRG4-encoding nucleic acids or fragments thereof. Such nucleic acids may be DNA, cDNA or RNA. Such RNA molecules can include siRNA and shRNA which modulate PRRG4 function.

As used herein the phrase "PRRG2 associated molecule" refers to a PRRG2 (also known as TMG2) protein, polypeptide or fragment thereof. The phrase also encompasses PRRG2-encoding nucleic acids or fragments thereof. Such nucleic acids may be DNA, cDNA or RNA. Such RNA molecules can include siRNA and shRNA which modulate PRRG2 function.

As used herein, the term "microarray" refers to an ordered arrangement of hybridizable array elements. The array elements are arranged so that there are preferably at least one or more different array elements, more preferably at least 100 array elements, and most preferably at least 1,000 array elements on a solid support. Preferably, the hybridization signal from each of the array elements is individually distinguishable, the solid support is a chip, and the array elements comprise oligonucleotide probes.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

As used herein, an "instructional material" includes a publication, a recording, a diagram, or any other medium of expression which can be used to communicate the usefulness of the composition of the invention for performing a method of the invention.

The phrase "solid support" refers to any solid surface including, without limitation, any chip (for example, silica-based, glass, or gold chip), glass slide, membrane, bead, solid particle (for example, agarose, sepharose, polystyrene or magnetic bead), column (or column material), test tube, or microtiter dish.

A "small molecule" can include chemicals isolated from combinatorial chemical libraries available from the pharmaceutical industry, nucleic acid molecules that function to down regulate PRRG4 expression, including antisense oligonucleotides, siRNA and shRNA.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. Constitutive promoters are functional in most or all tissues of an animal. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the animal compared to other parts of the animal. Temporally regulated promoters are functional only or predominantly during certain periods of animal development, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences.

I. Preparation of PRRG4-Related and PRRG2-Related Nucleic Acid Molecules, Proteins, and Antibodies Thereto A. Nucleic Acid Molecules Nucleic acid molecules encoding the PRRG4 or PRRG2 protein of the invention may be prepared by two general methods: (1) Synthesis from appropriate nucleotide triphosphates, or (2) Isolation from biological sources. Both methods utilize protocols well known in the art.

The availability of nucleotide sequence information, such as the full length cDNA having SEQ ID NO: 1 or SEQ ID NO: 11 (FIG. 8), enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector.

Nucleic acid sequences encoding PRRG4 or PRRG2 may be isolated from appropriate biological sources using methods known in the art. In a preferred embodiment, a cDNA clone is isolated from a cDNA expression library of human origin. In an alternative embodiment, utilizing the sequence information provided by the cDNA sequence, genomic clones encoding PRRG4 or PRRG2 may be isolated. Alternatively, cDNA or genomic clones having homology with PRRG4 may be isolated from other species, such as mouse, using oligonucleotide probes corresponding to predetermined sequences within the PRRG4 gene.

In accordance with the present invention, nucleic acids having the appropriate level of sequence homology with the protein coding region of SEQ ID NO: 1 or SEQ ID NO: 11 may be identified by using hybridization and washing conditions of appropriate stringency. For example, hybridizations may be performed, according to the method of Sambrook et al., (supra) using a hybridization solution comprising: 5×SSC, 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-65° in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{ Log } [Na+] + 0.41(\% G+C) - 0.63(\% \text{formamide}) - 600/\text{\#bp in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable E. coli host cell. Genomic clones of the invention encoding the human or mouse PRRG4 or PRRG2 gene may be maintained in lambda phage FIX II (Stratagene).

PRRG4- or PRRG2-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO: 1 or SEQ ID NO: 11. Such oligonucleotides are useful as probes for detecting or isolating PRRG4 genes.

It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, with respect to the PRRG4 sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a human population. Genetic polymorphisms giving rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in SEQ ID NO: 1 or SEQ ID NO: 11, or it may be a mutant, variant, derivative or allele of this sequence. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in SEQ ID NO: 1 or SEQ ID NO: 11 yet encode a polypeptide with the same amino acid sequence.

On the other hand, the encoded polypeptide may comprise an amino acid sequence which differs by one or more amino acid residues from the amino acid sequence shown in SEQ ID NO:2 or SEQ ID NO: 12. Nucleic acid encoding a polypeptide which is an amino acid sequence mutant, variant, derivative or allele of the sequence shown in SEQ ID NO: 2 or SEQ ID NO: 12 is further provided by the present invention. Nucleic acid encoding such a polypeptide may show greater than 60% homology with the coding sequence shown in SEQ ID NO: 1 or SEQ ID NO: 11, greater than about 70% homology, greater than about 80% homology, greater than about 90% homology or greater than about 95% homology.

Also within the scope of the invention are antisense oligonucleotide sequences based on the PRRG4 or PRRG2 nucleic acid sequences described herein. Antisense oligonucleotides may be designed to hybridize to the complementary sequence of nucleic acid, pre-mRNA or mature mRNA, interfering with the production of polypeptides encoded by a given DNA sequence (e.g. either native PRRG4 or PRRG2 polypeptide or a mutant form thereof), so that its expression is reduced or prevented altogether. In addition to the PRRG4 or PRRG2 coding sequence, antisense techniques can be used to target control sequences of the PRRG4 or PRRG2 gene, e.g. in the 5' flanking sequence of the PRRG4 or PRRG2 coding sequence, whereby the antisense oligonucleotides can interfere with PRRG4 or PRRG2 control sequences. The construction of antisense sequences and their use is described in Peyman and Ulman, Chemical Reviews, 90:543-584, (1990), Crooke, Ann. Rev. Pharmacol. Toxicol., 32:329-376, (1992), and Zamecnik and Stephenson, Proc. Natl. Acad. Sci., 75:280-284, (1974). As an alternative to antisense oligonucleotides, the invention also provides siRNA molecules which are effective to silence the expression of the PRRG4 or PRRG2 genes.

The present invention provides a method of detecting nucleic acid of interest, the method including hybridization of a probe having part or all of the sequence shown in SEQ ID NO: 1, SEQ ID NO: 11 or a complementary sequence, to target nucleic acid. Hybridization is generally followed by identification of successful hybridization and isolation of nucleic acid which has hybridized to the probe, which may involve one or more steps of PCR.

Such oligonucleotide probes or primers, as well as the full-length sequence (and mutants, alleles, variants, and derivatives) are useful in screening a test sample containing nucleic acid for the presence of alleles, mutants or variants, especially those that confer susceptibility or predisposition to cancers, the probes hybridizing with a target sequence from a sample obtained from the individual being tested. The conditions of the hybridization can be controlled to minimize non-specific binding, and preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the contiguous bases shown in SEQ ID NO: 1 or SEQ ID NO: 11, or any allele associated with cancer susceptibility, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of cancer susceptibility.

Methods involving use of nucleic acid in diagnostic and/or prognostic contexts, for instance in determining susceptibility to cancer, and other methods concerned with determining the presence of sequences indicative of cancer susceptibility are discussed below.

Nucleic acid according to the present invention may be used in methods of gene therapy, for instance in treatment of individuals with the aim of preventing or curing (wholly or partially) cancer. This too is discussed below.

B. Protein

PRRG4 and PRRG2 proteins are vitamin-K dependent transmembrane proteins which regulate oncogenic activity in mammals. A full-length PRRG4 or PRRG2 protein of the present invention may be prepared in a variety of ways, according to known methods. The protein may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding PRRG4 and PRRG2 enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of PRRG4 and/or PRRG2 may be produced by expression in a suitable prokaryotic or eukaryotic system. For example, part or all of a DNA molecule, such as the cDNA having SEQ ID NO: 1 or SEQ ID NO: 11, may be inserted into a plasmid vector adapted for expression in a bacterial cell, such as *E. coli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The PRRG4 or PRRG2 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as reticulocyte lysate.

A polypeptide according to the present invention may be used in screening for molecules which affect or modulate its activity or function. Such molecules may be useful in a therapeutic (possibly including prophylactic) context.

The present invention also provides antibodies capable of immunospecifically binding to proteins of the invention. Polyclonal antibodies directed toward PRRG4 and PRRG2 may be prepared according to standard methods. In a preferred embodiment, monoclonal antibodies are prepared, which react immunospecifically with various epitopes of PRRG4 and PRRG2. Monoclonal antibodies may be prepared according to general methods of Köhler and Milstein, following standard protocols. Polyclonal or monoclonal antibodies that immunospecifically interact with PRRG4 and/or PRRG2 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-PRRG4 and anti-PRRG2 antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

II. Uses of PRRG4- and PRRG2-Encoding Nucleic Acids, Proteins and Antibodies Thereto PRRG4 and PRRG2 are transmembrane proteins which play a role in malignant transformation. The PRRG4 and PRRG2 molecules of the invention may be used to advantage in genetic screening assays to identify those patients that may be at risk. The protein may also be used to follow patient response to tumor therapy as well as to indicate tumor progression. Screening assays may also be developed which assess PRRG4 and PRRG2 activity associated with tumor formation.

Additionally, PRRG4 and PRRG2 nucleic acids, proteins and antibodies thereto, according to this invention, may be used as a research tool to identify other proteins that are intimately involved in tumor progression. Biochemical elucidation of PRRG4 and PRRG2 activity will facilitate the development of these novel screening assays for assessing a patient's propensity for cancer. Such studies should result in the identification of efficacious agents for the detection and treatment of cancer.

A. PRRG4- and PRRG2 Encoding Nucleic Acids

PRRG4- and PRRG2-encoding nucleic acids may be used for a variety of purposes in accordance with the present invention. PRRG4- or PRRG2 encoding DNA, RNA, or fragments thereof may be used as probes to detect the presence of and/or expression of genes encoding PRRG proteins. Methods in which PRRG encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The PRRG-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, PRRG4- and PRRG2 encoding nucleic acids may be used to advantage to identify and characterize other genes of varying degrees of relation to PRRG4 and PRRG2, thereby enabling further characterization of the role these proteins play in tumorigenesis. Additionally, they may be used to identify genes encoding proteins that interact with PRRG4 and PRRG2 (e.g., by the "interaction trap" technique), which should further accelerate identification of the components involved in malignant progression and metastasis.

Nucleic acid molecules, or fragments thereof, encoding PRRG4 or PRRG2 may also be utilized to control the production of PRRG4 and PRRG2, thereby regulating the amount of protein available to participate in cellular signaling processes. Alterations in the physiological amount of PRRG4 or PRRG2 proteins may dramatically affect the activity of other protein factors involved in tumor formation.

The availability of PRRG4 and PRRG2 encoding nucleic acids enables the production of strains of laboratory mice which overexpress part, or all, of the PRRG4 or PRRG2 gene or mutated sequences thereof. Such mice provide an in vivo model for cancer. Alternatively, the PRRG4 and PRRG2 sequence information provided herein enables the production of knockout mice in which the endogenous gene encoding PRRG4 or PRRG2 has been specifically inactivated. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role PRRG4 and/or PRRG2 plays in embryonic development and cancer.

A transgenic mouse carrying the human PRRG4 or PRRG2 gene is generated by direct replacement of the mouse gene with the human gene. These transgenic animals are useful for drug screening studies as animal models for human diseases and for eventual treatment of disorders or diseases associated with biological activities modulated by PRRG4 or PRRG2. Alternatively, expression levels of PRRG4 or PRRG2 may be increased by heterologous overexpression of the encoding nucleic acid without replacement of the murine gene.

As a means to define the roles that PRRG4 and PRRG2 play in mammalian systems, mice may be generated that cannot make PRRG4 or PRRG2 protein because of a targeted mutational disruption of the PRRG4 or PRRG2 gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered PRRG4 or PRRG2 gene generally should not fully encode the same protein native to the host animal and its expression product should be altered to a minor or great degree, or absent altogether. However, it is conceivable that a more modestly modified gene will fall within the compass of the present invention if it is a specific alteration.

Figure 7:
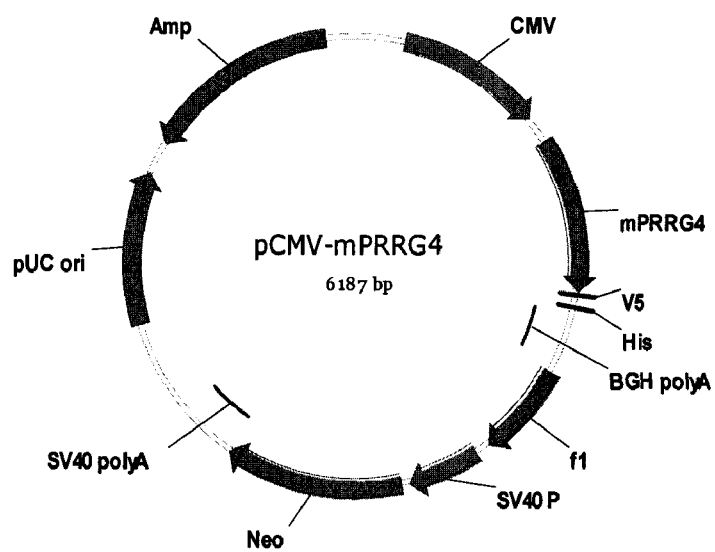
FIG. 7 is a schematic diagram of the vector utilized to create the transgenic mice of the invention.

The DNA used for altering a target gene may be obtained by a wide variety of techniques that include, but are not limited to, isolation from genomic sources, preparation of cDNAs from isolated mRNA templates, direct synthesis, or a combination thereof. An exemplary vector for this purpose is shown in FIG. 7.

A type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated PRRG4 or PRRG2 genes to selectively inactivate the wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Therapeutic agents for the treatment or prevention of cancer may be screened in studies using PRRG4 over-expressing transgenic mice of the invention.

In another embodiment of the invention, PRRG4 knockout mice may be used to produce an array of monoclonal antibodies specific for PRRG4 protein.

Finally, the invention also includes a "knockdown" mouse, wherein shRNA is expressed transgenically to down regulate PRRG4 expression levels.

As described above, PRRG4-encoding nucleic acids are also used to advantage to produce large quantities of substantially pure PRRG4 protein, or selected portions thereof. It should be noted that each of the above embodiments can also entail creating transgenic mice with over express or under express PRRG2.

B. PRRG4 and PRRG2 Protein and Antibodies

Purified PRRG4 or PRRG2, or fragments thereof, may be used to produce polyclonal or monoclonal antibodies which also may serve as sensitive detection reagents for the presence and accumulation of such proteins (or complexes containing the same) in mammalian cells. Recombinant techniques enable expression of fusion proteins containing part or all of the PRRG4 or PRRG2 protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for PRRG4 or PRRG2 may be used in a variety of assays designed to detect and quantitate the proteins. Such assays include, but are not limited to: (1) flow cytometric analysis; (2) immunochemical localization of the proteins in tumor cells; and (3) immunoblot analysis (e.g., dot blot, Western blot) of extracts from various cells. Additionally, as described above, antibodies can be used for purification of PRRG4 and PRRG2 (e.g., affinity column purification, immunoprecipitation).

From the foregoing discussion, it can be seen that PRRG4- and PRRG2 associated molecules, including, without limitation, nucleic acids, vectors, proteins and antibodies of the invention can be used to detect PRRG4 and/or PRRG2 gene expression and alter PRRG4 or PRRG2 protein accumulation for purposes of assessing the genetic and protein interactions involved in malignant transformation.

Exemplary approaches for detecting PRRG4 or PRRG2 nucleic acid or polypeptides/proteins include:

a) comparing the sequence of nucleic acid in the sample with the PRRG4 or PRRG2 nucleic acid sequence to determine whether the sample from the patient contains mutations; or b) determining the presence, in a sample from a patient, of the polypeptide encoded by the PRRG4 and/or PRRG2 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal PRRG4 or PRRG4 gene or from known mutations thereof; or, d) using a specific binding member capable of binding to a PRRG4 or PRRG2 nucleic acid sequence (either normal sequence or known mutated sequence), the specific binding member comprising nucleic acid hybridizable with the PRRG4 or PRRG2 sequence, or substances comprising an antibody domain with specificity for a native or mutated PRRG4 or PRRG2 nucleic acid sequence or the polypeptide encoded by it, the specific binding member being labeled so that binding of the specific binding member to its binding partner is detectable; or, e) using PCR involving one or more primers based on normal or mutated PRRG4 or PRRG2 gene sequences to screen for normal or mutant PRRG4 or PRRG2 genes in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the PRRG4 or PRRG2 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the PRRG4 and PRRG2 genes and their association with cancer paves the way for aspects of the present invention to provide the use of materials and methods, such as are disclosed and discussed above, for establishing the presence or absence in a test sample of the gene, or an allelic variant specifically associated with cancer. This may be for diagnosing a predisposition of an individual to cancer. Alternatively, it may be for diagnosing cancer of a patient with the disease as being associated with the gene.

This allows for planning of appropriate therapeutic and/or prophylactic measures, permitting stream-lining of treatment. The approach further streamlines treatment by targeting those patients most likely to benefit.

According to another aspect of the invention, methods of screening drugs for cancer therapy to identify suitable drugs for inhibiting PRRG4 or PRRG2 product functions are provided.

The PRRG4 or PRRG2 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a PRRG4 or PRRG2 polypeptide or fragment and the agent being tested, or examine the degree to which the formation of a complex between a PRRG4 or PRRG2 polypeptide or fragment and a known ligand is interfered with by the agent being tested.

Molecular modeling should facilitate the identification of specific organic molecules with capacity to bind to the active site of the protein based on conformation or key amino acid residues required for function. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

Another technique for drug screening provides high throughput screening for compounds having suitable binding affinity to the PRRG4 or PRRG2 polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with PRRG4 or PRRG2 polypeptide and washed. Bound PRRG4 or PRRG2 polypeptide is then detected by methods well known in the art.

Purified PRRG4 or PRRG2 can be coated directly onto plates for use in the aforementioned drug screening techniques. However, non-neutralizing antibodies to the polypeptide can be used to capture antibodies to immobilize the polypeptide on the solid phase.

This invention also contemplates the use of competitive drug screening assays in which neutralizing antibodies capable of specifically binding the PRRG4 or PRRG2 polypeptide compete with a test compound for binding to the polypeptide or fragments thereof. In this manner, the antibodies can be used to detect the presence of any peptide which shares one or more antigenic determinants of the PRRG4 or PRRG2 polypeptide.

A further technique for drug screening involves the use of host eukaryotic cell lines or cells (such as described above) which have a nonfunctional PRRG4 or PRRG2 gene. These host cell lines or cells are defective at the polypeptide level. The host cell lines or cells are grown in the presence of drug compound. The rate of growth of the host cells is measured to determine if the compound is capable of regulating the growth, or altering the morphology of PRRG4 or PRRG2 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, one first determines the three-dimensional structure of a protein of interest (e.g., PRRG4 or PRRG2 polypeptide) or, for example, PRRG4 or PRRG2 protein complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., PRRG4 polypeptide) may be analyzed by an alanine scan (Wells, 1991) Meth. Enzym. 202:390-411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., altered PRRG4 or PRRG2 polypeptide activity or stability or which act as inhibitors, agonists, antagonists, etc. of polypeptide activity. By virtue of the availability of cloned PRRG4 and PRRG2 sequences, sufficient amounts of the PRRG4 or PRRG2 polypeptide may be made available to perform such analytical studies as x-ray crystallography. In addition, the knowledge of the PRRG4 and PRRG2 protein sequences provided herein will guide those employing computer modeling techniques in place of, or in addition to x-ray crystallography.

III Therapeutics

A. Pharmaceuticals and Peptide Therapies

The PRRG4 and PRRG2 polypeptides/proteins, antibodies, peptides and nucleic acids of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

B. Methods of Gene Therapy

As a further alternative, the nucleic acid encoding the authentic biologically active PRRG4 or PRRG2polypeptide could be used in a method of gene therapy, to treat a patient who is unable to synthesize the active "normal" polypeptide or unable to synthesize it at the normal level, thereby providing the effect elicited by the wild-type proteins and suppressing the abnormal function of "aberrant" protein. Alternatively, vectors could be designed which encode siRNAs capable of silencing PRRG4 or PRRG2. Such vectors may prove efficacious in methods for inhibiting tumor formation mediated by PRRG4 or PRRG2.

Vectors such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide or the encoded siRNA. The transfected nucleic acid may be permanently incorporated into the genome of each of the targeted tumor cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, lentiviruses, herpes viruses including HSV and EBV, adenoviruses, and retroviruses. Many gene therapy protocols in the prior art have employed disabled murine retroviruses.

The following examples are provided to illustrate certain embodiments of the invention. They are not intended to limit the invention in any way.

Examples

PRRG4- and PRRG2-New Markers for Malignant Transformation

In accordance with the present invention, we have elucidated the function of a previously uncharacterized protein called PRRG4 (also referred to as TMG-4). PRRG4 is the first vitamin-K dependent transmembrane protein identified to date which regulates oncogenic activity in mammals. Thus, the invention provides diagnostic tools and biomarkers in novel methods to detect and treat human malignancies.

Figure 2A:
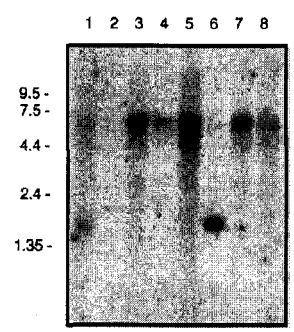
FIG. 2A depicts a Northern blot showing analysis of total RNA from human tissues using a radio-labeled DNA full-length cDNA probe against the prrg4 mRNA, shows high level of expression in placenta (lane 3), liver (lane 5), kidney (lane 7) and skeletal muscle in lane 6. Heart (lane 1), brain (lane 2), lung (lane 4) and pancreas (lane 8) show lower level prrg4 expression.
Figure 2B:
FIG. 2B depicts a multiple mouse tissue blot using a murine prrg4 cDNA probe, and shows high level expression in stomach (lane 7) and lungs (lane 3). The brain (lane 1), heart (lane 2), liver (lane 4), spleen (lane 5), stomach (lane 7), small intestine (lane 8), skeletal muscle (lane 9), testis (lane 11) and uterus (lane 12) showed significantly lower levels of endogenous prrg4 expression.

PRRG4, a transmembrane protein, has homology to vitamin K dependent clotting factors. The deduced amino acid sequence is 226 residues long (for the human protein). The putative transmembrane domain spans residues 114-138. The protein also contains a potential SH3 domain-binding motif PXXP in residues 176-179, and a WW domain interaction motif PPXY at residues 204-207. See FIG. 1. In humans, it is expressed in placenta, lung, liver, skeletal muscle, and kidney. It has a similar tissue distribution in the mouse. See FIGS. 2A and 2B.

Northern analysis (FIG. 2A and FIG. 2B) of total RNA from human tissues using a radio-labeled DNA full-length cDNA probe against prrg4 mRNA shows essentially ubiquitous expression. In FIG. 1A, high levels of expression are observed in placenta (lane 3), liver (lane 5), kidney (lane 7) and skeletal muscle in lane 6. Heart (lane 1), brain (lane 2), lung (lane 4) and pancreas (lane 8) show lower levels of prrg4 expression. Moreover, when the tissue distribution of prrg4 was compared against tissue specific levels of several known Gla-containing proteins, the broad tissue distribution of prrg4 (See FIG. 2D) suggests a multi-faceted role for this protein, distinguishing it from other vitamin-K dependent proteins, i.e., those involved in coagulation or bone formation (data not shown).

The mouse prrg4 which shares 78% sequence identity with its human homolog however showed a similar expression profile on a multiple tissue blot (FIG. 2b) with a very high signal in placental tissue (lane 13) followed by thymus (lane 10), kidney (lane 6).

In additional experiments, PRRG4 and PRRG2 mRNA levels were assessed in 31 different human cell lines. The highest expression was observed in mammary gland (T47D, ZR75-1, MDA-MB-453, MDA-361, and DU4475) and in prostate carcinoma cell lines (LNCaP and PC-3). See FIG. 2C. FIG. 2D is a graph depicting PRRG4 and PRRG2 mRNA levels in 31 human tissues.

The prrg4 Gene is a Highly Conserved Gene Among Vertebrates

In humans prrg4 is located on the p-arm of Chromosome 11 (11p3). The gene is made of 6 exons with a total transcript length of 1964 bases resulting in a protein with 226 aminoacids (26 kDa). While there are apparent orthologs of prrg4 in most of the model vertebrates (Table 1), the human genome itself consists of a paralog on chromosome 19, designated prrg2, with a 52% homology. The prrg2 transcript encodes a 202 amino acid long protein.

TABLE 1

Cross-species comparison of exons, transcripts and protein length encoded by prrg4

| Species | Common name | Exons | mRNA | Protein |
| --- | --- | --- | --- | --- |
| Homo sapien | Human | 6 | 1964 | 226 |
| Bos Taurus | Cow | 5 | 684 | 228 |
| Canis familaris | Dog | 5 | 678 | 225 |
| Mus musculus | Mouse | 6 | 2670 | 226 |
| Danio rerio | Zebrafish | 6 | 633 | 210 |
| Pan troglodytes | Chimpanzee | 6 | 1967 | 226 |
| Macaca mulatta | Rhesus monkey | 5 | 675 | 224 |
| Monodelphis domestica | Opossom | 5 | 681 | 226 |
| Takifugu rubripes | Pufferfish | 4 | 540 | 180 |
| Xenopus tropicalis | African frog | 5 | 654 | 218 |
| Gallus gallus | Chicken | 6 | 1308 | 227 |
| Ciona intestinalis | Sea squirt (Chordata) | 6 | 662 | 169 |
| Rattus norvegicus | Rat | 5 | 681 | 226 |
| Gasterosteus aculeatus | Stickleback fish | 6 | 880 | 205 |
| Tetraodon nigroviridis | Spotted pufferfish | 4 | 522 | 174 |

We queried an online database, Human Protein Atlas on the world wide web at proteinatlas.org/index.php, for tissues and cells stained by anti PRRG4 antibody. Staining was generally widespread and weak thus suggesting a housekeeping-like function for this protein.

In particular, a strong staining in certain CNS neuronal cells (e.g. Purkinje cells) and in a cell line derived from a medulloblastoma tumor (D341Med) appears indicative of an involvement of the PRRG4 protein in tumorigenesis in these tissues. Moreover, PRRG4 antibody also stains either strongly or moderately in colorectal, pancreatic, and liver tumors as well as normal hepatocytes and glandular cells of colon, intestine, rectum, and stomach.

In the same database, and in contrast, PRRG2 staining is relatively weak, is not overlapping and is only observed in a few cell lines and tumor samples.

In an attempt to characterize PRRG4 in vivo functions, we assessed expression levels in breast tumor samples (commercially available from Ambion). Quantitative real-time PCR experiments consistently demonstrated a significantly reduced level of expression of PRRG4 in the breast tumor sample when compared to its normal adjacent tissue, however this appears to be a feature of the Ambion samples. In additional studies, we assessed levels of PRRG4 expression levels in uterus, ovarian, breast and lung tissue samples which were obtained from several Cooperative Human Tissue Network (CHTN) divisions including Eastern and Midwestern divisions. The tissues were processed to extract total RNA. Only the tissues with matching normal adjacent tissue were selected for this study. Real-time PCR was used to compare the expressions of PRRG2 and PRRG4 in the Tumor vs adjacent tissue.

The results of our studies are presented in the Tables below.

| PRRG4 fold increase in tumor vs. normal adjacent tissues | | | | | |
|---|---|---|---|---|---|
| | 1.5-3 times | 3-5 times | 5-20 times | >20 times | Total |
| Uterus | 2 | 1 | 4 | 5 | 12 |
| Ovarian | 2 | 0 | 3 | 2 | 7 |
| Breast | 3 | 2 | 0 | 1 | 6 |
| Lung | 2 | 1 | 3 | 0 | 6 |

| PRRG2 fold increase in tumor vs. normal adjacent tissues | | | | | |
|---|---|---|---|---|---|
| | 1.5-3 times | 3-5 times | 5-20 times | >20 times | Total |
| Uterus | 2 | 1 | 5 | 6 | 14 |
| Ovarian | 1 | 2 | 1 | 2 | 6 |
| Breast | 2 | 2 | 2 | 1 | 7 |
| Lung | 5 | 0 | 1 | 0 | 6 |

| Summary and Summary Ratio | | | | | |
|---|---|---|---|---|---|
| | Number of Samples | PRRG4↑ | PRRG2↑ | PRRG4↑ or PRRG2↑ | PRRG4↑ & PRRG2↑ |
| Uterus | 15 | 12 (80) | 14 (93.33) | 15 (100) | 12 (73.33) |
| Ovarian | 8 | 7 (87.5) | 3 (75) | 7 (87.5) | 7 (75) |
| Breast | 10 | 6 (60) | 7 (70) | 8 (80) | 6 (50) |
| Lung | 13 | 7 (46.15) | 6 (46.15) | 7 (53.84) | 6 (38.46) |

All of the uterus carcinoma tissues (100%) demonstrate elevated PRRG4 or PRRG2 compared to the normal adjacent tissue. Fold increase rates are provided in the summary table. For these patients 12 out of 15 showed increased PRRG4 levels, while 14 out of 15 showed increased PRRG2 expression. 7 out of 8 ovarian patients has increased PRRG4 expression in tumors. While breast and lung patients exhibit the same levels of elevated expression in almost half of the patients tested, we observed an increased PRRG4 in both cases. 80% of the patients with breast cancer showed increased PRRG4 or PRRG2 expression. 53% of lung cancer patients were observed to have increased PRRG4 or PRRG2.

Human PRRG4-GFP Fusion Protein Localizes to the Trans-Golgi Network

Figure 3:
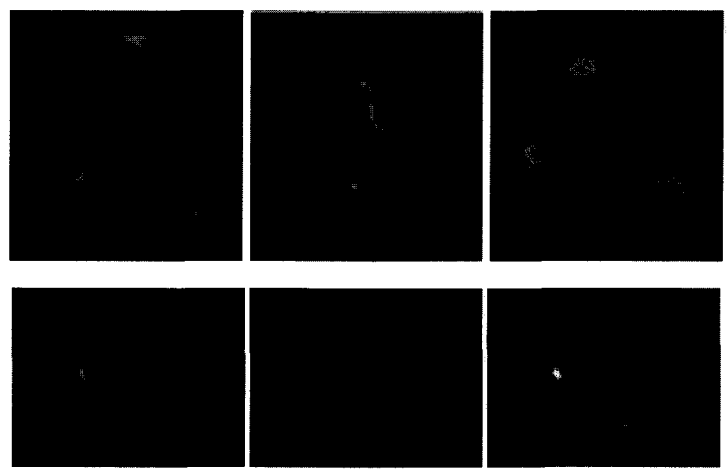
FIG. 3 shows the results of experiments with C-terminal GFP fusions of human PRRG4 which localized the chimeric protein to the trans-golgi assembly in HEK293 cells. Juxtanuclear localization of human-PRRG4-GFP fusion protein (top, left), human-PRRG4-GFP fusion closeup (top, center), GFP only control (top, right) is also shown. The hPRRG4-GFP colocalizes with Golgi specific protein (bottom, right). The left and center images in the lower panel correspond to hPRRG4-GFP only and Golgi-specific staining only.

A human PRRG4 mammalian expression plasmid, phPRRG4-GFP was generated to localize PRRG4 in tissue culture. Full length PRRG4 cDNA was isolated by RACE PCR from a commercially available full length cDNA library. The cDNA was cloned in pcDNA-CT-GFP plasmid (Invitrogen) to obtain a complete human PRRG4 protein with a C-terminal GFP fusion. HEK 293 cells were transfected with phPRRG4-GFP by Lipofectamine mediated transfection and GFP expression was observed under fluorescence microscopy 48 h post transfection. We observed that the PRRG4-GFP fusion protein was primarily localized around the nucleus. When the transfected cells were stained for a golgi specific marker, the GFP signal colocalized with the golgi marker suggesting that PRRG4 is localized to the golgi. (FIG. 3). Furthermore, immunoprecipitation experiments using a GST-PRRG4 fusion protein identified NipSnap4 protein as a strong binder (protein sequence identified by mass spectrophotometry). NipSnap4 is a vesicular chaperone protein involved in intra and inter vesicular trafficking and is known to localize in the golgi-endoplasmic reticulum assembly.

RNA Interference Knocks Down Human-prrg4 Expression by >80%

To facilitate functional analysis of PRRG4, stable clones of HEK293 cells over-expressing mouse PRRG4 tagged with a V5 epitope were established by transfecting HEK293 cells with pmPRRG4-V5 plasmid. Mouse PRRG4 cDNA was isolated from a commercially available mouse liver cDNA library by RACE PCR and cloned into pcDNA3.1-V5 plasmid backbone to generate pmPRRG4-V5. The transfectants were grown under Hygromycin selection for several weeks to obtain stable clones of HEK293 cells overexpressing mPRRG4-V5. Eight siRNA pairs (see table) were designed against mPRRG4 and tested in HEK293 cells stably overexpressing mPRRG4-V5. Initial screens identified 3 siRNA pairs to knockdown >80% of mPRRG4 expression. These siRNA sequences were used to generate corresponding shRNA (short hairpin RNA) expression vector is a commercial pSilencer backbone (Ambion Inc.).

PRRG4

| siRNA Target Sequence | Region | Start | GC Content |
|---|---|---|---|
| GCCTAAAGGATTCCGAACA | ORF | 424 | 47.37% (SEQ ID NO: 3) |
| ACAATAGGTTTGATCTAGA | ORF | 508 | 31.58% (SEQ ID NO: 4) |
| CAATAGGTTTGATCTAGAA | ORF | 509 | 31.58% (SEQ ID NO: 5) |
| ATAGGTTTGATCTAGAACT | ORF | 511 | 31.58% (SEQ ID NO: 6) |
| TAGGTTTGATCTAGAACTC | ORF | 512 | 36.84% (SEQ ID NO: 7) |
| GAGAGTGCTATGAGGAGTT | ORF | 553 | 47.37% (SEQ ID NO: 8) |
| TGAGGAGTTCTGTAGTTAT | ORF | 563 | 36.84% (SEQ ID NO: 9) |
| GCCTTCTGACTGGATTGAT | ORF | 700 | 47.37% (SEQ ID NO: 10) |

Figure 4:
FIG. 4 shows the knockdown efficiencies of the three shRNA constructs (in lanes 2, 3 and 4).

Stable HEK293 cells were transfected with three different shRNA constructs and cultured for 48 hours post transfection. The cells were then harvested and total lysates were run on a 4-12% polyacrylamide gel (reducing). Western analysis was carried out using anti-V5-HRP antibodies to estimate PRRG4-V5 levels in different lysates. FIG. 4 shows the knockdown efficiencies of the three shRNA constructs (in lanes 2, 3 and 4). Our results indicate that shRNA in lane 2 demonstrated the highest levels of PRRG4 knockdown (ca 80%) when compared to the untransfected control in lane 1. The three bands indicate the three different states of processing for PRRG4.

PRRG4 Knockdown Induces Hyperphosphorylation of ERK 1/2

Figure 5A:
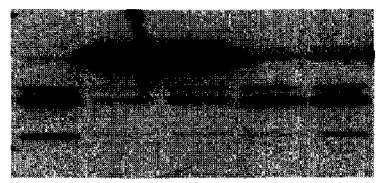
FIG. 5A is a Western blot showing that PRRG4 knockdown induces hyperphosphorylation of ERK 1/2.

In this experiment, we show that shRNA-mediated knockdown of PRRG4 in HEK293 stable clones induces a 500-fold hyperphosphorylation of signaling proteins ERK 1 and 2 (lanes 2 and 3) while there was no change in activated ERK in untransfected cells (lanes 1, 4 and 5) as detected by anti-phospho-ERK antibodies in total cellular lysates. The fold increase of activated ERK over unphosphorylated ERK was calculated by densitometric analysis. See FIG. 5A.

ERK 1 and 2 are involved in signal transduction leading to cellular proliferation and their aberrant activation may interfere with ERK mediated signal transduction into the nucleus thus resulting in hyperphosphorylated ERK proteins. ERK proteins are critical for cellular proliferation and apoptosis and play a major role in balancing events that may either lead to neoplastic growth or cell death. We believe that accumulation of activated ERK proteins in response to a drastic decrease in PRRG4 levels is an indicator of the ability of this protein to modulate ERK activity into tumor suppression or oncogenesis.

ERK1/2 can be activated by various treatments like FBS, PMA or EGF in the 293 cell line that is stably transfected with mPRRG4. When PRRG4 is knocked down in these cells by shRNA against PRRG4, and treatments like EGF, PMA or FBS are used to activate ERK1/2, higher ERK1/2 activation can be observed compared to that of control cells where no shRNA is used. There appears to be crosstalk between PRRG4 signaling pathway and the signaling pathways that are activated by PMA, EGF or FBS. Although PRRG4 knockdown by shRNA further increases the amount of activated ERK1/2 levels, Akt activation is not affected in the same cells. This result strengthens the possibility of specific crosstalk between ERK1/2 signaling and PRRG4. See FIG. 5B.

In additional experiments, the effects of down modulation of PRRG2 in an adenocarcinoma cell line (HEC1B) were assessed. Cells were treated with the siRNAs listed below Qiagen (HP GenomeWide siRNA).

```
Hs_PRRG2_1:
The sense strand is:
r(CAG UGA GGA GAC AGA CCA A)dTdT    (SEQ ID NO: 13)

antisense:
r(UUG GUC UGU CUC CUC ACU G)dGdG    (SEQ ID NO: 14)

modifications:
none

Hs_PRRG2_2:
The sense:
r(GGG AGA GCU ACA UCU ACA A)dTdT    (SEQ ID NO: 15)

antisense:
r(UUG UAG AUG UAG CUC UCC C)dAdA    (SEQ ID NO: 16)

modifications:
none
```

Two separate transfection protocols were employed (Oligofectamine from Invitrogen and Hiperfect transfection reagent Qiagen) and comparable results on ERK phosphorylation were obtained. At 48 hours, the siRNAs against both PRRG4 or PRRG2 increased ERK phosphorylation 3-6 fold. The percent phosphorylation compared to negative siRNA (non silencing control siRNA from Qiagen) is listed at the bottom of FIG. 5C.

PRRG4 can Interact with Several Proteins that May Regulate Cell Proliferation

PRRG4 has one WW-binding domain in its cytosolic domain. WW domains are involved in several cellular processes including cell cycle control and cell proliferation. In order to analyze the possible interactions of PRRG4 with different WW motif containing proteins, the cytosolic domain of human PRRG4 was purified by our group and used in TranSignal WW Domain Arrays. This array contains WW domains from 67 different human proteins and each WW domain is spotted in duplicate. Cytosolic domain of PRRG4 was shown to bind WW domain of several proteins in this array (FIGS. 6A and 6B). Among these proteins Yes-Associated Protein1 (YAP 1) and Nedd4 are particularly important as they are known to play essential roles in several cellular activities including cell proliferation. The Hits from Protein Array tables provided below show the proteins that are used on the array.

The cystosolic domain of hPPRG4 was expressed in insect cells and proteins were purified by HA and histidine columns. Interactions of cytosolic hPPRG4 with different SH3 and WW domains were tested by incubating purified hPRRG4 proteins with arrays containing SH3 and WW domains of several proteins. After incubation, PRRG4 bound to several proteins, most of which are non-receptor tyrosine kinases or scaffolding proteins. A list of hits is shown in the Table below. These newly identified binding partners provide valuable therapeutic targets for the isolation and characterization of therapeutic agents that impact PRRG4 mediated oncogenesis.

Hits from Protein Array
SH3 Array

| | |
|---|---|
| Abl2 | Abelson-related protein; Arg tyrosine kinase |
| HCK | Hemopoietic cell kinase: SRC Kinase |
| Lyn | Src family of non-receptor protein Tyrosine kinase |
| OSF | OSF: Osteoclast stimulating factor 1 |
| Tec | Tyrosine-protein kinase Tec |
| BTK | Bruton Tyrosine Kinase |
| GRB2 | Growth factor receptor-bound protein 2 (weak binding) |
| NEBL | Nebulette |
| Grap-D2 | Grb2-related adaptor protein, SH3 Domain #2 |
| Y124 | PAK-interacting exchange factor beta |
| PEXD | Peroxisomal membrane protein PEX13 |

WW Array

| | |
|---|---|
| YAP1 | YES-ASSOCIATED PROTEIN 1, |
| NEDD4 | Ubiquitin-protein ligase Nedd-4 |
| NEDD4L | NEDD4-like ubiquitin ligase 3 |
| NEDL1 | NEDD4-like ubiquitin ligase 1 |
| MAGI-3 | Membrane-associated guanylate kinase-related MAGI-3 |
| WWP1-D1 | Nedd-4-like ubiquitin-protein ligase (Atropin-1-interacting protein 5) |
| ITCH | atrophin-1 interacting protein 4 |
| TAZ | transcriptional co-activator with PDZ-binding motif (TAZ) |

Transgenic PRRG4 Over-Expressing Mice Develop Malignancies

We explored the role of PRRG4 in vivo by generating transgenic mice that overexpressed the murine prrg4 gene. The mammalian over-expression cassette was generated by cloning the prrg4 cDNA in an expression vector, pcDNA3.1 purchased from Invitrogen. The terminal stop codon was removed by polymerase chain reaction and the resulting cDNA was ligated into the pcDNA expression vector. Removal of the stop codon allows readthrough of the transcript into the C-terminal V5-epitope coding sequence in the vector backbone to result in expression of PRRG4-V5 fusion protein. See FIG. 7. The expression cassette was sequenced to confirm accuracy of sequence and the vector was renamed pCMV-mPRRG4-V5. A linear expression cassette (1.56 kb) was generated by digesting pCMV-mPRRG4-V5 with MfeI and DraIII restriction endonucleases and purified on a 1% agarose gel. The expression cassette DNA was then purified on QiaEx gel extraction columns (Qiagen). This DNA was microinjected into the mouse zygote at the University of Pennsylvania Transgenic Mouse facility The PRRG4 over-expressing (high PRRG4) mice were maintained under observation for 18-20 mos of age.

We identified 8 sick mice from the colonies for necropsy. 7 out of 8 mice had visible tumors in a variety of organ systems like kidney, liver, lungs, spleen, GI tract, and the heart. The discovery of proto-oncogenic activity of PRRG4 has utility in the prediction, early detection and treatment of malignancies of the breast, prostate and the hematopoietic system.

Based on this unexpected result, we did an in silico screen of multiple human cell lines to look for those that overexpressed PRRG4. Two tumor cell lines, one a prostate cancer line, the other a breast tumor line, expressed levels of PRRG4 transcript 8-10 fold higher than most other cell lines. Additional results are presented in FIG. 2C. Thus, the present invention identifies PRRG4 as a proto-oncogene whose overexpression results in malignancies in animal models. Accordingly methods and compositions for screening for agents which perturb the tumor-promoting function of PRRG4 are provided. Also provided are agents so identified. Based on the data obtained herein, it appears that blocking PRRG4 synthesis or function will decrease the likelihood of tumor formation, and may also result in death of tumor cells.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of detecting a predisposition to cancer in a patient, the method comprising the steps of:
   (a) providing a biological sample from the patient; and
   (b) detecting expression levels of a PRRG4 nucleic acid in the biological sample compared to a normal control sample, wherein samples exhibiting elevated levels in PRRG4 nucleic acid expression relative to the normal control sample, are indicative of an increased predisposition to cancer in said patient, wherein said cancer is selected from the group consisting of kidney, liver, lung, spleen, GI tract, heart, prostate, neuronal, colorectal, pancreatic, colon, intestine, rectum, stomach, breast, uterus, and ovarian cancer.

2. The method as claimed in claim 1, wherein said PRRG4 nucleic acid is selected from the group consisting of a PRRG4 nucleic acid of SEQ ID NO: 1 or fragments of SEQ ID NO: 1.

3. The method as claimed in claim 1, wherein said detection is performed using an agent having binding affinity for said PRRG4 nucleic acid, said agent comprising a detectable label.

4. The method as claimed in claim 3, wherein said detectable label is selected from the group consisting of fluorescein, rhodamine, phycoerythrin, biotin, and streptavidin.

5. The method as claimed in claim 1, wherein said biological sample is selected from the group consisting of colon tissue, breast tissue, uterine tissue, ovarian tissue, brain tissue, prostate tissue, hematopoietic cells, lung, stomach, pancreas, kidney, liver, heart, and cervix and said normal control sample is obtained from normal adjacent tissue.

6. The method as claimed in claim 1, wherein said detection comprises:
   a) extracting nucleic acids from said biological sample;
   b) contacting said extracted nucleic acid with oligonucleotide primers which specifically hybridize to PRRG4 encoding nucleic acids if any are present;
   c) subjecting said extracted nucleic acid and primers to conditions suitable for polymerase chain reaction amplification; and
   d) assessing the resulting reaction product for amplified PRRG4 nucleic acid, relative to PRRG4 nucleic acid levels present in the normal control sample.

7. The method as claimed in claim 6, wherein said reaction product is assessed by a method selected from the group consisting of gel electrophoresis, restriction digest mapping, scintillation counting, quantitative real time PCR, and filter paper assays.

8. The method as claimed in claim 7, wherein said primers comprise a detectable label.

9. The method as claimed in claim 8, wherein said detectable label is selected from the group consisting of chemiluminescent, enzymatic, radioactive, fluorescent, biotin, and streptavidin.

10. The method of claim 1, wherein said patient diagnosed with cancer and is undergoing treatment for cancer.

11. The method as claimed in claim 6, wherein said method for detecting PRRG4 encoding nucleic acid in a biological sample as a tumor marker for cancer comprises a method to monitor residual disease or recurrence of malignancy.

12. The method of claim 1, wherein the detection step further comprises:
   (i) contacting a PRRG4 gene with a probe specific for the gene under conditions in which the probe specifically hybridizes to the gene to form a stable hybridization complex; and
   (ii) detecting the hybridization complex.

13. The method of claim 12, performed on a microarray.

14. The method of claim 1 further comprising assessing expression levels of PRRG2 nucleic acid of SEQ ID NO: 11 or fragments of SEQ ID NO: 11 in the biological sample relative to the normal control sample, wherein said cancer is selected from the group consisting of lung, ovarian, breast and uterine cancer.

15. The method of claim 6, wherein said oligonucleotide primers specifically hybridize to PRRG4 nucleic acids under moderate stringency conditions.

* * * * *

SEQUENCE LISTING

<160> NUMBER OF SEQ ID NOS: 16

<210> SEQ ID NO 1
<211> LENGTH: 2015
<212> TYPE: DNA
<213> ORGANISM: Homo sapiens

<400> SEQUENCE: 1

```
cccggaccga ggcaggacct caccccgcgc gtgttccccg ggcgcccctc tgcgaacccc      60
aggcccttcc caggtttgcg cgcggggcc atccagaccc tgcggagagc gaggcccgga     120
gcgtcgccga ggtttgaggg cgccggagac cgagggcctg gcggccgaag gaaccgcccc     180
aagaagagcc tctggcccgg gggctgctgg aacatgtgcg gggggacaca gtttgtttga     240
cagttgccag actatgttta cgcttctggt tctactcagc caactgccca cagttaccct     300
ggggtttcct cattgcgcaa gaggtccaaa ggcttctaag catgcgggag aagaagtgtt     360
tacatcaaaa gaagaagcaa acttttttcat acatagacgc cttctgtata atagatttga     420
tctggagctc ttcactcccg gcaacctaga aagagagtgc aatgaagaac tttgcaatta     480
tgaggaagcc agagagattt ttgtggatga agataaaacg attgcatttt ggcaggaata     540
ttcagctaaa ggaccaacca caaaatcaga tggcaacaga gagaaaatag atgttatggg     600
ccttctgact ggattaattg ctgctggagt attttttggtt attttttggat tacttggcta     660 ctatctttgt atcactaagt gtaataggct acaacatcca tgctcttcag ccgtctatga     720 aaggggagg cacactccct ccatcatttt cagaagacct gaggaggctg ccttgtctcc     780
attgccgcct tctgtggagg atgcaggatt accttcttat gaacaggcag tggcgctgac     840
cagaaaacac agtgtttcac caccaccacc atatcctggg cacacaaaag gatttaggtt     900
atttaaaaaa tctatgtctc tcccatctca ctgactacct tgtcattttg gtataagaaa     960
tttgtgttat tgataggcc gggcatggtg gctcatgcct gtaatcccag cactttggga    1020
ggccaggagt tcgagaccag cctggccaac atggtgaaac ccggtctcta ctaaaaattc    1080
aaaaattacc taggcgtcat ggggcatgcc tgtagtccca cctacttggg aggctgaagc    1140
aggagaattg ctcgaacctg ggaggcagag gttgcagtaa gctgagatca cgccactgca    1200
ttccagcctg ggcgacagag caagactcca tctcaaaaat aaaataaaaa aagaaagaaa    1260
```

```
gaaaagaaga agaaaagaga agaaggagaa ggagatgaag gaggaggagg aggagaagga      1320
gaagaagaag aagaagaaga ccacaaaaga catgactatc caacttttta tgacaaactg      1380
caaggaataa aggaagaata agtccatgta ctgtaccaca gaagttctgt ctgcatcttg      1440
gacctgaact tgatcattat cagcttgata agagactttt tgactctata tccttgcagt      1500
taagaagaaa gcactttttt gtaatgtttg ttttaatggt tcaaaaaaaa tctttcttat      1560
aaagagcata ggtagaatta gtgaactctt tggatccttt gtacagataa aggttataga      1620
tttcttgtgt tgaatattaa aaagcaagg atgtctaacc attaagatta tccaaagtca       1680
ggctgggcgc agtggctcac gcctgtaatc ccagcacttt gggagggata ggtgggcgga      1740
tcacctgagg tcaggagttt gagaccagcc tggccaacat ggcaaaaccc cgtctctaca      1800
aaaatacaaa agaaattagc cagacatgat ggcgggtgcc tctaatccca gctactgggg      1860
aggctgaggt gggagaatcg cttgaactcg ggaggtggag gttgtagtga ggcgagattg      1920
tgccattgca ctccaacctg ggcgacagag tgagactcca tctcaaaaaa aaaaaaaaaa      1980
aaaaaaaaaa aaaaaaaaaa aaaaaaaaaa aaaaa                                 2015
```

<210> SEQ ID NO 2
<211> LENGTH: 226
<212> TYPE: PRT
<213> ORGANISM: Homo Sapiens

<400> SEQUENCE: 2

```
Met Phe Thr Leu Leu Val Leu Leu Ser Gln Leu Pro Thr Val Thr Leu
 1               5                  10                  15

Gly Phe Pro His Cys Ala Arg Gly Pro Lys Ala Ser Lys His Ala Gly
             20                  25                  30

Glu Glu Val Phe Thr Ser Lys Glu Glu Ala Asn Phe Phe Ile His Arg
         35                  40                  45

Arg Leu Leu Tyr Asn Arg Phe Asp Leu Glu Leu Phe Thr Pro Gly Asn
     50                  55                  60

Leu Glu Arg Glu Cys Asn Glu Glu Leu Cys Asn Tyr Glu Glu Ala Arg
 65                  70                  75                  80

Glu Ile Phe Val Asp Glu Asp Lys Thr Ile Ala Phe Trp Gln Glu Tyr
                 85                  90                  95

Ser Ala Lys Gly Pro Thr Thr Lys Ser Asp Gly Asn Arg Glu Lys Ile
            100                 105                 110

Asp Val Met Gly Leu Leu Thr Gly Leu Ile Ala Ala Gly Val Phe Leu
        115                 120                 125

Val Ile Phe Gly Leu Leu Gly Tyr Tyr Leu Cys Ile Thr Lys Cys Asn
    130                 135                 140

Arg Leu Gln His Pro Cys Ser Ser Ala Val Tyr Glu Arg Gly Arg His
145                 150                 155                 160

Thr Pro Ser Ile Ile Phe Arg Arg Pro Glu Ala Ala Leu Ser Pro
                165                 170                 175

Leu Pro Pro Ser Val Glu Asp Ala Gly Leu Pro Ser Tyr Glu Gln Ala
            180                 185                 190

Val Ala Leu Thr Arg Lys His Ser Val Ser Pro Pro Pro Tyr Pro
        195                 200                 205

Gly His Thr Lys Gly Phe Arg Val Phe Lys Lys Ser Met Ser Leu Pro
    210                 215                 220

Ser His
225
```

```
<210> SEQ ID NO 3
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 3
gcctaaagga ttccgaaca                                               19

<210> SEQ ID NO 4
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 4
acaataggtt tgatctaga                                               19

<210> SEQ ID NO 5
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 5
caataggttt gatctagaa                                               19

<210> SEQ ID NO 6
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 6
ataggtttga tctagaact                                               19

<210> SEQ ID NO 7
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 7
taggtttgat ctagaactc                                               19

<210> SEQ ID NO 8
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 8
gagagtgcta tgaggagtt                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic Sequence
```

-continued

```
<400> SEQUENCE: 9
tgaggagttc tgtagttat                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 10
gccttctgac tggattgat                                                19

<210> SEQ ID NO 11
<211> LENGTH: 1411
<212> TYPE: DNA
<213> ORGANISM: Homo Sapiens

<400> SEQUENCE: 11
gccagaaacg gggatcaggc ctggttaccg ggagtggggc gcccctcctc cttatcccct    60
cccctcttcc ctgtcccctt tcacagctgg ctgtagctgg ccaaggagtt ctcgattaaa   120
gaggaagggg cagtgctcac atttctgggc aggtgtctgg aaaatatgag gggccacccc   180
tctctgctgc tgctatatat ggcattaacc acctgcctgg atacttcacc cagtgaggag   240
acagaccaag aagtcttcct gggtccccca gaggcccaga gcttcctgag tagccatacc   300
cggattccaa gagccaacca ctgggacctg gagctgctca caccagggaa cctggaacgg   360
gagtgtctgg aagagaggtg ttcctgggaa gaggccaggg agtattttga ggacaacact   420
ctcacggagc gcttttggga gagctacatc tacaatggca aggagggcg tggacgagtg   480 gatgtggcca gcctggctgt ggggctgaca ggtggcatcc tgctcattgt cctggccggc   540
ctgggagcct tttggtatct cgcctggcga cagcaccgag ccagcagcc ctgtccccaa    600 gaggccgggc tcattagccc tctgagtcct ttgaaccctc tgggcccacc gacgcccctg   660
cctccacccc cacccccacc cccaggcctc ccacctatg agcaggcgct ggcagcctct   720
ggggtacacg acgcacctcc acccccctac accagcctca ggaggcctca ctgaagagct   780
gctttcgaga cccggctctc cgaaccgtgc ccctgattca taccggattc cggaagccgc   840
taggcctcat agacgccgaa gctggacttg gagtggggaa tggtgggagt aggggtcatc   900
cggcccgagg cctgccctgg cacacgcgtt tccgccgcgt atggatatac acatgttttc   960
ggcaacgtgt tcccgtgtcc tggcccctca cgggccccca cactctcctg accgtgaggg  1020
cactggtcag ttccgccccc gtggtaggca gacgcgcggg gaaattcgga cccaggagcc  1080 cagcccggc tgtgccatct tgtgtatggg cagatatgac ctgacagccc cctccagtgc   1140
cacagggtac gcacacgcag agcccgcct gtgcacacgc gtgtcttcgt gcactccccg   1200
tgcggtacag gggcacttcg taacccaggg aaagggcggg gggcatattt gcaagcgcgc  1260
tcggtgcggg caggctcgca ttgcacccag ggagctggag ttgagctgtt cccctaaata  1320 aaaaccctc ggaaaggaga ccaaaaaaag cagaaataat gcaaaaaata ataatgaaat   1380
gaactgcgat cccaaaaaaa aaaaaaaaaa a                                  1411

<210> SEQ ID NO 12
<211> LENGTH: 202
<212> TYPE: PRT
<213> ORGANISM: Homo Sapiens

<400> SEQUENCE: 12
```

```
Met Arg Gly His Pro Ser Leu Leu Leu Tyr Met Ala Leu Thr Thr
 1               5                  10                  15

Cys Leu Asp Thr Ser Pro Ser Glu Glu Thr Asp Gln Glu Val Phe Leu
             20                  25                  30

Gly Pro Pro Glu Ala Gln Ser Phe Leu Ser Ser His Thr Arg Ile Pro
             35                  40                  45

Arg Ala Asn His Trp Asp Leu Glu Leu Leu Thr Pro Gly Asn Leu Glu
 50                  55                  60

Arg Glu Cys Leu Glu Glu Arg Cys Ser Trp Glu Ala Arg Glu Tyr
 65                  70                  75                  80

Phe Glu Asp Asn Thr Leu Thr Glu Arg Phe Trp Glu Ser Tyr Ile Tyr
                 85                  90                  95

Asn Gly Lys Gly Gly Arg Gly Arg Val Asp Val Ala Ser Leu Ala Val
                100                 105                 110

Gly Leu Thr Gly Gly Ile Leu Leu Ile Val Leu Ala Gly Leu Gly Ala
            115                 120                 125

Phe Trp Tyr Leu Arg Trp Arg Gln His Arg Gly Gln Gln Pro Cys Pro
    130                 135                 140

Gln Glu Ala Gly Leu Ile Ser Pro Leu Ser Pro Leu Asn Pro Leu Gly
145                 150                 155                 160

Pro Pro Thr Pro Leu Pro Pro Pro Pro Pro Pro Gly Leu Pro
                165                 170                 175

Thr Tyr Glu Gln Ala Leu Ala Ala Ser Gly Val His Asp Ala Pro Pro
                180                 185                 190

Pro Pro Tyr Thr Ser Leu Arg Arg Pro His
                195                 200

<210> SEQ ID NO 13
<211> LENGTH: 21
<212> TYPE: DNA
<213> ORGANISM: Artificial Sequence
<220> FEATURE:
<223> OTHER INFORMATION: siRNA

<400> SEQUENCE: 13
cagugaggag acagaccaat t                                          21

<210> SEQ ID NO 14
<211> LENGTH: 21
<212> TYPE: DNA
<213> ORGANISM: Artificial Sequence
<220> FEATURE:
<223> OTHER INFORMATION: siRNA

<400> SEQUENCE: 14
uuggucuguc uccucacugg g                                          21

<210> SEQ ID NO 15
<211> LENGTH: 21
<212> TYPE: DNA
<213> ORGANISM: Artificial Sequence
<220> FEATURE:
<223> OTHER INFORMATION: siRNA

<400> SEQUENCE: 15
gggagagcua caucuacaat t                                          21

<210> SEQ ID NO 16
<211> LENGTH: 21
<212> TYPE: DNA
<213> ORGANISM: Artificial Sequence
```

```
<220> FEATURE:
<223> OTHER INFORMATION: siRNA

<400> SEQUENCE: 16
uuguagaugu agcucuccca a                                              21
```